United States Patent
Truneh et al.

(10) Patent No.: US 12,247,075 B2
(45) Date of Patent: Mar. 11, 2025

(54) BTN3A BINDING PROTEINS AND USES THEREOF

(71) Applicants: IMCHECK THERAPEUTICS SAS, Marseilles (FR); INSTITUT JEAN PAOLI & IRENE CALMETTES, Marseilles (FR); CENTRE NATIONAL DE LA RECHERCHE SCIENTIFIQUE—CNRS, Paris (FR); INSERM (INSTITUT NATIONAL DE LA SANTÉ ET DE LA RECHERCHE MÉDICALE), Paris (FR); UNIVERSITÉ D'AIX-MARSEILLE, Marseilles (FR)

(72) Inventors: Alemseged Truneh, Sudbury, MA (US); Christine Pasero, Marseilles (FR); René Hoet, Marseilles (FR); Magali Colazet, Marseilles (FR); Daniel Olive, Marseilles (FR)

(73) Assignees: IMCHECK THERAPEUTICS SAS, Marseilles (FR); INSTITUT JEAN PAOLI & IRENE CALMETTES, Marseilles (FR); CENTRE NATIONAL DE LA RECHERCHE SCIENTIFIQUE—CNRS, Paris (FR); INSERM (INSTITUT NATIONAL DE LA SANTE ET DE LA RECHERCHE MEDICALE), Paris (FR); UNIVERSITE D'AIX-MARSEILLE, Marseilles (FR)

( * ) Notice: Subject to any disclaimer, the term of this patent is extended or adjusted under 35 U.S.C. 154(b) by 931 days.

(21) Appl. No.: 17/418,017

(22) PCT Filed: Dec. 26, 2019

(86) PCT No.: PCT/EP2019/087040
§ 371 (c)(1),
(2) Date: Jun. 24, 2021

(87) PCT Pub. No.: WO2020/136218
PCT Pub. Date: Jul. 2, 2020

(65) Prior Publication Data
US 2022/0073619 A1    Mar. 10, 2022

(30) Foreign Application Priority Data
Dec. 26, 2018  (EP) ..................................... 18306845

(51) Int. Cl.
*C07K 16/28*  (2006.01)
*C12N 15/63*  (2006.01)

(52) U.S. Cl.
CPC .......... *C07K 16/2827* (2013.01); *C12N 15/63* (2013.01); *C07K 2317/24* (2013.01); *C07K 2317/565* (2013.01); *C07K 2317/622* (2013.01); *C07K 2317/75* (2013.01); *C07K 2317/92* (2013.01)

(58) Field of Classification Search
CPC ...... C07K 16/2827; C12N 15/63; A61P 35/00
See application file for complete search history.

(56) References Cited

U.S. PATENT DOCUMENTS

| | | | |
|---|---|---|---|
| 2014/0322235 A1* | 10/2014 | Olive | A61P 31/00 530/389.6 |
| 2015/0139997 A1* | 5/2015 | Vermot-Desroches | A61P 31/12 530/387.3 |
| 2015/0323643 A1 | 11/2015 | Hill et al. | |
| 2018/0340031 A1* | 11/2018 | Yamniuk | C07K 16/2887 |

FOREIGN PATENT DOCUMENTS

| | | | |
|---|---|---|---|
| WO | 2012/080351 A1 | 6/2012 | |
| WO | WO-2012080769 A1 * | 6/2012 | .............. A61P 31/00 |

OTHER PUBLICATIONS

Christelle Harly, et al, "Key implication of CD277/butyrophilin-3 (BTN3A) in cellular stress sensing by a major human γσ T-cell subset", Blood (2012) 120 (11): 2269-2279. https://doi.org/10.1182/blood-2012-05-430470 (Year: 2012).*
Palakodeti, A., Sandstrom, A., Sundaresan, L., Harly, C., Nedellec, S., Olive, D., . . . & Adams, E. J. "The Molecular Basis for Modulation of Human Vg9Vd2 T Cell Responses by CD277/Butyrophilin-3 (BTN3A)-specific Antibodies". J. Biol. Chem., 287(39); 09, 2012). https://doi.org/10.1074/jbc.m112 (Year: 2012).*
Protein Data Bank in Europe, EMBL-EBI, Crystal Structure of the Human BTN3A1 Ectodomain in Complex with the 103.2 Single Chain Antibody, https://www.ebi.ac.uk/pdbe/entry/pdb/4F9P, Released: Aug. 8, 2012 (Year: 2012).*
Hanf, K. et al., "Antibody humanization by redesign of complementarity-determining region residues proximate to the acceptor framework". Methods, 65 (2014) 68-76. (Year: 2014).*
Anonymous: "Antibody Humanization Service", https://www.genscript.com/Antibody-Humanization.html, Feb. 28, 2016.
Harly et al: "Key implication of CD277/butrophilin-3 (BTN3A) in cellular stress sensing by a major human ?? T-cell subset", Blood, vol. 120, No. 11, pp. 2269-2279, Sep. 13, 2012.

(Continued)

*Primary Examiner* — Julie Wu
*Assistant Examiner* — Sonia Jessica Laurie
(74) *Attorney, Agent, or Firm* — WC&F IP

(57) ABSTRACT

It is disclosed anti-BTN3A activating antibody fragments that specifically bind to BTN3A and activate the cytolytic function of Vγ9/Vδ2 T cells. The disclosure more specifically relates to specific anti-BTN3A binding proteins comprising such activating antibody fragments and their use in the manufacturing of novel drugs for use in treating cancer disorders, in particular cancers susceptible to be treated with activated γδ T cells.

9 Claims, No Drawings
Specification includes a Sequence Listing.

(56) References Cited

OTHER PUBLICATIONS

Palakodeti et al: "The Molecular Basis for Modulation of Human V[gamma]9V[delta]2 T Cell Responses by CD277/Butyrophilin-3 (BTN3A)-specific Antibodies", Journal of Biological Chemistry, vol. 287, No. 39, pp. 32780-32790, Sep. 21, 2012.

Protein Data Bank in Europe: "103.2 antibody-BTN3A1 antibody fragment in PDB entry 4f9p < PDB3 < EMBL-EBI", https://www.dbi.ac.uk/pdbe/entry/pdb/4f9p/protein/2, Aug. 8, 2012.

* cited by examiner

BTN3A BINDING PROTEINS AND USES THEREOF

INTRODUCTION

To date, various therapeutic and vaccine strategies have been proposed that rely on a modulation of T cells; several immunomodulatory antibodies to CTLA-4, PD-1 and PD-L1 have already been approved for clinical use by multiple regulatory agencies throughout the world. Although these drugs represent major advances in cancer therapy, there still remain unmet medical needs for large parts of cancer patient populations that do not respond to the currently available treatments.

BTN3A1, BTN3A2 and BTN3A3 isoforms are expressed on lymphoid cells and peripheral blood mononuclear cells (PBMCs). In addition, literature and database analysis indicates that BTN3A members are widely expressed in various tumors of haematological origin such as acute myeloid leukaemia (AML), and in solid tumors such as breast, colon, ovarian, in gastric cancer and pancreatic ductal adenocarcinoma (PDAC). Immunohistochemical analysis of PDAC tissues confirmed BTN3A expression in all tested tumor samples, whereas it was either absent or barely detectable in control pancreatic normal tissue. Furthermore, it has been shown by immunohistochemistry that epithelial BTN3A expression was significantly associated with better prognosis in high grade serious epithelial ovarian cancer patients and correlated with a higher density of infiltrating T cells.

In addition, analysis of expression signatures from ~18,000 human tumors with overall survival outcomes across 39 malignancies, identified tumor-infiltrating γδ T cells (typically Vγ9Vδ2 T cells) as the most significant favourable cancer-wide prognostic signature (Gentles et al., 2015). These data have been confirmed by a recent study showing that abundance of tumor infiltrating Vγ9Vδ2 T lymphocytes is associated with favourable outcome in cohorts of patients with colorectal or prostate adenocarcinoma or haematological malignancies (Tosolini et al., 2017).

Studies have shown that anti-BTN3A antibodies bound to target cells trigger activation of Vγ9Vδ2 T cells derived from solid tumors (for a review see Blazquez et al., 2018). Given the strong potential of γδ T cells (typically Vγ9Vδ2 T cells) for anti-tumor response, the BTN3A-antibody-mediated priming and sensitization of tumor cells for killing by Vγ9Vδ2 T cells constitutes an attractive and novel therapeutic opportunity to treat cancer, for both solid and haematological malignancies.

The patent publications WO 2012080351, EP2651441, EP2946791, US20140322235, WO2012080769 refer to various antibodies against CD277 able to activate or inhibit the cytolytic function, cytokine production and proliferation of Vγ9Vδ2 T cells.

In particular, WO2012080769 describes specific monoclonal murine antibodies referred such as mAb 20.1 and 7.2 with the capacity to activate the cytolytic function, cytokine production and proliferation of Vγ9Vδ2 T cells and their use in treating cancer and infection disorders. Additionally, WO2012080769 describes a specific murine monoclonal antibody referred as mAb 103.2 having the opposite activity of inhibiting the cytolytic function, production and proliferation of Vγ9Vδ2 T cells. Consequently, such murine antibody mAb 103.2, and corresponding chimeric and humanized versions were suggested to be useful in treating inflammatory disorders.

Palakodeti et al., 2012 describes scFv fragment of mAb 103.2 (Journal of biological chemistry, 287 (39) pages 32780-32790).

The inventors now surprisingly found that some fragments of mAb 103.2, such as the Fab or F(ab')$_2$ fragment exhibit activating properties with respect to BTN3A and are capable of activating the cytolytic function, cytokine production and/or proliferation of Vγ9Vδ2 T cells.

Therefore, the present disclosure relates to BTN3A binding proteins comprising such activating antibody fragments of mAb 103.2 and their use in the manufacturing of novel drugs for use in treating cancer disorders, in particular cancers susceptible to be treated with activated γδ T cells (typically Vγ9Vδ2 T cells).

SUMMARY

The present disclosure relates to an isolated BTN3A binding protein, comprising at least a BTN3A antibody fragment having
  i. a heavy chain variable region (VH) comprising H-CDR1 of SEQ ID NO:1, H-CDR-2 of SEQ ID NO:2, and H-CDR3 of SEQ ID NO:3; and,
  ii. a light chain variable region (VL) comprising a L-CDR1 of SEQ ID NO:4, a L-CDR2 of SEQ ID NO:5 or SEQ ID NO:17, and a L-CDR3 of SEQ ID NO:6; and wherein said BTN3A binding protein has the following properties:
    i. it binds to human BTN3A1 with a $K_D$ of 10 nM or less, preferably with a $K_D$ of 5 nM or less as measured by bio-layer interferometry (BLI) technology, and/or,
    ii. it induces the activation of γδ T cells (such as Vγ9Vδ2 T cells) in co-culture with cancer cells, such as Daudi or SKOV-3 cells, with an $EC_{50}$ of 10 nM or below, preferably of 1 nM or below, as measured in a CD107 degranulation assay, and/or
    iii. it induces the activation and proliferation of γδ T cells (typically Vγ9Vδ2 T cells) within PBMCs.

In specific embodiments, said BTN3A antibody fragment comprises
  (i) a heavy chain variable region of SEQ ID NO:18, and,
  (ii) a light chain variable region of SEQ ID NO:19.

In specific embodiments that may be combined with the previous embodiments, said anti-BTN3A antibody fragment is selected from scFv, Fab, or (Fab)'$_2$ fragment.

In specific embodiments that may be combined with the previous embodiments, said BTN3A binding protein of the present disclosure is monovalent or bivalent for its binding to BTN3A.

In specific embodiments that may be combined with the previous embodiments, said BTN3A binding protein of the present disclosure essentially consists of the BTN3A antibody fragment selected from scFv, Fab, or F(ab)'$_2$ fragment, for example it consists of an scFv comprising a VH domain of SEQ ID NO:18 and a VL domain of SEQ ID NO:19.

In specific embodiments that may be combined with the previous embodiments, said BTN3A binding protein is a fusion protein comprising said BTN3A antibody fragment fused to one or more additional protein domains.

Said BTN3A binding protein may be used as a medicament, for example, in the treatment of a cancer, typically cancers susceptible of being treated with γδ T cells (typically Vγ9Vδ2 T cells).

In specific embodiments that may be combined with the previous embodiments, said BTN3A binding protein may be used in the treatment of (i) a solid tumor and/or (ii) a haematological cancer.

The disclosure thus also relates to a pharmaceutical composition comprising the BTN3A binding protein as above defined, in combination with one or more of a pharmaceutically acceptable excipient, diluent or carrier, optionally comprising other active ingredients.

The disclosure further provides an expression vector for the recombinant production of a BTN3A binding protein as above defined, in a host cell, comprising one or more nucleic acids encoding said anti-BTN3A binding protein.

In specific embodiments, said nucleic acids encoding said anti-BTN3A binding protein comprise the coding sequences of heavy and light chains of said BTN3A antibody fragment as above defined, typically SEQ ID NOs:18 and 19.

The disclosure also pertains to a host cell comprising an expression vector as above defined.

Also, part of the present disclosure is a process for the production of a BTN3A binding protein as above defined, comprising: (i) culturing the host cell as above defined for expression of said protein by the host cell; optionally (ii) purifying said protein and formulating said protein.

Another aspect of the disclosure relates to a method for inducing ex vivo or in vivo the proliferation and/or activation of γδ T cells (typically Vγ9Vδ2 T cells), said method comprising contacting an efficient amount of a BTN3A binding protein as above defined, with said γδ T cells (typically Vγ9Vδ2 T cells), optionally in the presence of other BTN3A expressing cells, such as BTN3A expressing tumor cells.

DETAILED DESCRIPTION

Definitions

In order that the present disclosure may be more readily understood, certain terms are first defined. Additional definitions are set forth throughout the detailed description.

As used herein, the term "BTN3A" has its general meaning in the art and refers to human BTN3A polypeptides including either BTN3A1 of SEQ ID NO:23, BTN3A2 of SEQ ID NO:24 or BTN3A3 of SEQ ID NO:25.

"Polypeptide," "peptide" and "protein," are used interchangeably and refer broadly to a polymer of amino acid residues of any length, regardless of modification (e.g., phosphorylation or glycosylation). The terms apply to amino acid polymers in which one or more amino acid residue is an analogue or mimetic of a corresponding naturally occurring amino acid, as well as to naturally occurring amino acid polymers. The terms apply to amino acid polymers in which one or more amino acid residue is an artificial chemical mimetic of a corresponding naturally occurring amino acid, as well as to naturally occurring amino acid polymers and non-naturally occurring amino acid polymer. Polypeptides can be modified, e.g., by the addition of carbohydrate residues to form glycoproteins. The terms "polypeptide," "peptide" and "protein" expressly include glycoproteins, as well as non-glycoproteins. In specific embodiments, the term "polypeptide" and "protein" refers to any polypeptide or protein which can be encoded by a gene and translated using cell expression system, such as mammalian host cell by recombinant means.

The term "recombinant protein", as used herein, includes proteins that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) proteins isolated from a host cell transformed to express the corresponding protein, e.g., from a transfectoma, etc.

The term "antibody" as used herein refers to immunoglobulin molecules and immunologically active portions of immunoglobulin molecules, i.e., molecules that contain an antigen binding site that specifically binds an antigen.

In natural antibodies of rodents and primates, two heavy chains are linked to each other by disulfide bonds, and each heavy chain is linked to a light chain by a disulfide bond. There are two types of light chains, lambda (l) and kappa (κ). There are five main heavy chain classes (or isotypes) which determine the functional activity of an antibody molecule: IgM, IgD, IgG, IgA and IgE. Each chain contains distinct sequence domains. In typical IgG antibodies, the light chain includes two domains, a variable domain (VL) and a constant domain (CL). The heavy chain includes four domains, a variable domain (VH) and three constant domains (CH1, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, transplacental mobility, complement binding, and binding to Fc receptors (FcR).

The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from nonhypervariable or framework regions (FR) can participate in the antibody binding site, or influence the overall domain structure and hence the combining site. Complementarity Determining Regions or CDRs refer to amino acid sequences which together define the binding affinity and specificity of the natural Fv region of a native immunoglobulin binding site. The light and heavy chains of an immunoglobulin each have three CDRs, designated L-CDR1, L-CDR2, L-CDR3 and H-CDR1, H-CDR2, H-CDR3, respectively. An antigen-binding site, therefore, typically includes six CDRs, comprising the CDRs set from each of a heavy and a light chain V region. Framework Regions (FRs) refer to amino acid sequences interposed between CDRs. Accordingly, the variable regions of the light and heavy chains typically comprise 4 framework regions and 3 CDRs of the following sequence: FR1-CDR1-FR2-CDR2-FR3-CDR3-FR4.

The residues in antibody variable domains are conventionally numbered according to a system devised by Kabat et al. This system is set forth in Kabat et al., 1987, in Sequences of Proteins of Immunological Interest, US Department of Health and Human Services, NIH, USA (Kabat et al., 1992, hereafter "Kabat et al."). This numbering system is used in the present specification. The Kabat residue designations do not always correspond directly with the linear numbering of the amino acid residues in SEQ ID sequences. The actual linear amino acid sequence may contain fewer or additional amino acids than in the strict Kabat numbering corresponding to a shortening of, or insertion into, a structural component, whether framework or complementarity determining region (CDR), of the basic variable domain structure. The correct Kabat numbering of residues may be determined for a given antibody by alignment of residues of homology in the sequence of the antibody with a "standard" Kabat numbered sequence. The CDRs of the heavy chain variable domain are located at residues 31-35 (H-CDR1), residues 50-65 (H-CDR2) and residues 95-102 (H-CDR3) according to the Kabat numbering system. The CDRs of the light chain variable domain are located at residues 24-34 (L-CDR1), residues 50-56 (L-CDR2) and residues 89-97 (L-CDR3) according to the Kabat numbering system.

As used herein the term "antibody fragment", more particularly refers to the antigen-binding domain of an antibody as disclosed herein. Antibody fragments include, but are not limited to, Fv, Fab, F(ab')$_2$, Fab', dsFv, scFv, sc(Fv)$_2$ and diabodies, VHH, etc. The term "$K_{assoc}$" or "$K_a$", as used herein, is intended to refer to the association rate of a particular antibody-antigen interaction, whereas the term "$K_{dis}$" or "$K_d$," as used herein, is intended to refer to the dissociation rate of a particular antibody-antigen interaction.

The term "$K_D$", as used herein, is intended to refer to the dissociation constant, which is obtained from the ratio of $K_d$ to $K_a$ (i.e. $K_d/K_a$) and is expressed as a molar concentration (M). $K_D$ values for antibodies can be determined using methods well established in the art. A method for determining the $K_D$ of a protein or an antibody is by using surface plasmon resonance, for example by using a biosensor system such as a Biacore® system. A simple binding interaction analysis by surface plasmon resonance (SPR) requires immobilization of the ligand to the sensor chip surface, followed by addition of the analyte of interest to the buffer flowing over the ligand surface. The interaction of the ligand and analyte is measured by the SPR instrument (typically the Biacore® system) as a change in refractive index over time. From this, the association ($K_a$) or dissociation ($K_d$) and equilibrium dissociation ($K_D$) constants can be derived. Affinity, and in particular the $K_D$ can also be assessed by the Octet® system. The Octet® platform is based on bio-layer interferometry (BLI) technology. The principle of BLI technology is based on the optical interference pattern of white light reflected from two surfaces—a layer of immobilized protein and an internal reference layer. The binding between a ligand immobilized on the biosensor tip surface and an analyte in solution produces an increase in optical thickness at the biosensor tip, which results in a shift in the interference pattern measured in nanometers. The wavelength shift (Δλ) is a direct measure of the change in optical thickness of the biological layer, when this shift is measured over a period of time and its magnitude plotted as a function of time, a classic association/dissociation curve is obtained. This interaction is measured in real-time, allowing to monitor binding specificity, association rate and dissociation rate, and concentration. (see Abdiche et al. 2008 but also the details in the results). Affinity measurements are typically performed at 25° C.

As used herein, the term "binding specificity" refers to the ability of an antibody to detectably bind to an antigen recombinant polypeptide, such as recombinant BTN3A1 polypeptide, with a $K_D$ of 100 nM or less, 10 nM or less, 5 nM or less, as measured by Surface Plasmon Resonance (SPR) measurements, for example as determined in the Examples (see Tables 1, 2, 4, 5 and 6) or by bio-layer interferometry (BLI) technology. In some embodiments, the antibody binds to BTN3A1 with a $K_D$ comprised between $10^{-3}$ pM and 100 nM, notably comprised between 10 pM and 100 nM, notably between 10 pM and 100 nM, or between $10^{-3}$ pM and 10 nM, notably 1 pM and 10 nM, notably between 10 pM and 10 nM, or between 1 pM and 5 nM, notably 10 pM and 5 nM or 100 pM and 5 nM as measured by SPR. In other embodiments, the antibody binds to BTN3A1 with a $K_D$ comprised between $10^{-3}$ pM and 100 nM, notably comprised between 10 pM and 100 nM, notably between 10 pM and 100 nM, or between $10^{-3}$ pM and 10 nM, notably 1 pM and 10 nM, notably between 10 pM and 10 nM, or between 1 pM and 5 nM, notably 10 pM and 5 nM or 100 pM and 5 nM as measured by bio-layer interferometry (BLI) technology.

An antibody that "cross-reacts with an antigen other than BTN3A" is intended to refer to an antibody that binds that antigen other than BTN3A with a $K_D$ of 10 nM or less, 1 nM or less, or 100 pM or less. An antibody that "does not cross-react with a particular antigen" is intended to refer to an antibody that binds to that antigen, with a $K_D$ of 100 nM or greater, or a $K_D$ of 1 μM or greater, or a $K_D$ of 10 μM or greater, said affinity being measured for example using similar Surface Plasmon Resonance (SPR) measurements or, using bio-layer interferometry (BLI) technology, as disclosed in the Examples. In certain embodiments, such antibodies that do not cross-react with the antigen exhibit essentially undetectable binding against these proteins in standard binding assays.

The isolated BTN3A binding protein according to the present disclosure refers to a protein that has binding specificity to BTN3A. A BTN3A binding protein may have cross-reactivity to other antigens, such as related BTN3A molecules from other species. Moreover, an isolated BTN3A protein may be substantially free of other cellular material and/or chemicals.

The phrases "an antibody recognizing an antigen" and "an antibody having specificity for an antigen" are used interchangeably herein with the term "an antibody which binds specifically to an antigen".

Specificity can further be exhibited by, e.g., an about 10:1, about 20:1, about 50:1, about 100:1, 10.000:1 or greater ratio of affinity/avidity in binding to the specific antigen versus nonspecific binding to other irrelevant molecules (in this case the specific antigen is a BTN3A polypeptide). The term "affinity", as used herein, means the strength of the binding of an antibody to an epitope. Affinity is typically assessed by the $K_D$ value of the antibody for BTN3A1.

The present disclosure relates to the unexpected finding that certain fragments of BTN3A binding antibodies (derived from mAb 103.2), previously known for its inhibiting properties towards BTN3A, exhibit activating properties. Such fragments with activating properties include Fab and F(ab')$_2$ fragments of mAb 103.2. The present disclosure further provides humanized versions of such mAb 103.2 antibody fragments exhibiting similar activating properties.

"Humanized antibody" as used herein, refers broadly to include antibodies made by a non-human cell having variable and constant regions which have been altered to more closely resemble antibodies that would be made by a human cell. For example, by altering the non-human antibody amino acid sequence to incorporate amino acids found in human germline immunoglobulin sequences. The humanized antibodies of the invention may include amino acid residues not encoded by human germline immunoglobulin sequences (e.g., mutations introduced by random or site-specific mutagenesis in vitro or by somatic mutation in vivo), for example in the CDRs.

In specific embodiments, the term "humanized antibody", as used herein, also includes antibodies in which CDR sequences derived from the germline of another mammalian species, such as a mouse, have been grafted onto human framework sequences. In other specific embodiments, the term "humanized antibody", as used herein, also includes antibodies in which H-CDR1 of SEQ ID NO:1, H-CDR2 of SEQ ID NO:2, H-CDR3 of SEQ ID NO:3, L-CDR1 of SEQ ID NO:4, L-CDR2 of SEQ ID NO:5 or 17, and L-CDR3 of SEQ ID NO:6 have been grafted onto human framework sequences.

As used herein, the term "activating antibody" refers to an antibody able to directly or indirectly induce immune functions of effector cells, for example to induce proinflammatory, cytolytic and/or immune responses. In particular, as used herein, an activating BTN3A antibody fragment has at least the capacity to induce the activation of γδ T cells (typically Vγ9Vδ2 T cells) in co-culture with cancer cells (such as Daudi cells and/or SKOV-3 cells), with an $EC_{50}$ of 10 nM or below, preferably of 1 nM or below, for example, 0.1 nM or below, as measured in a CD107 degranulation assay, for example as described in the Examples below. Thus as per the present application, the $EC_{50}$ (half maximal effective concentration) is established in a dose response curve and represents the concentration of activating BTN3A antibody fragment where 50% of the maximal effect (i.e.: the maximal proportion of activated Vγ9Vδ2 T cells) is observed. As indicated in the example, assessment of the Vγ9Vδ2 T cells cytotoxicity is performed by evaluating CD107 receptor at their membrane surface by flow cytometry. Dose-response curve are typically established by quantifying CD107 positive Vγ9Vδ2 T cells after 4 h of co-culture with Daudi or SKOV-3 cells in presence of the antibody fragments at 37° C. In some embodiments, the $EC_{50}$ is comprised between $10^{-4}$ nM and 10 nM, notably between $10^{-4}$ nM and 1 nM, notably between $10^{-4}$ nM and 0.1 nM, or between $10^{-3}$ nM and 10 nM, $10^{-3}$ nM and 1 nM or between $10^{-3}$ nM and 0.1 nM.

As used herein, the term "subject" includes any human or non-human animal. The term "non-human animal" includes all vertebrates, e.g., mammals and non-mammals, such as non-human primates, sheep, dogs, cats, horses, cows, chickens, amphibians, reptiles, etc.

An effect of an antibody fragment as per the present application on proliferation and/or activation can also be tested typically by incubation of PBMCs with said antibody fragments. Immune cells proliferation and activation can be then followed typically by flow cytometry. For example, several cell generations can be traced using dye dilution of CellTrace violet Dye™ used for in vitro labelling of cells. Incubation of antibody fragments at a concentration of 60 nM (±20%) at 37° C. with PBMCs for 5 days can typically lead to a significant proliferation of Vγ9Vδ2 T cells (leading for example to an increase of at least 20% notably at least 30 or 35% of the total Vγ9Vδ2 T cell population).

Activation of γδ T cells (typically Vγ9Vδ2 T cells) can be followed by assessing the proportion of Vγ9Vδ2 T cells expressing the activation marker CD25. Typically, a significant increase in the proportion of Vγ9Vδ2 T cells expressing the activation marker CD25 is observed.

As used herein, the term, "optimized" means that a nucleotide sequence has been altered to encode an amino acid sequence using codons that are preferred in the production cell or organism, generally a eukaryotic cell, for example, a Chinese Hamster Ovary cell (CHO) or a human cell. The optimized nucleotide sequence is engineered to retain completely or as much as possible the amino acid sequence originally encoded by the starting nucleotide sequence. The amino acid sequences encoded by optimized nucleotide sequences are also referred to as optimized.

As used herein, the percent identity between the two sequences is a function of the number of identical positions shared by the sequences (i. e., % identity=number of identical positions/total number of positions×100), taking into account the number of gaps, and the length of each gap, which need to be introduced for optimal alignment of the two sequences. The comparison of sequences and determination of percent identity between two sequences can be accomplished using a mathematical algorithm, as described below.

The percent identity between two amino acid sequences can be determined using the Needleman and Wunsch algorithm (NEEDLEMAN, and Wunsch).

The percent identity between two nucleotide or amino acid sequences may also be determined using for example algorithms such as EMBOSS Needle (pair wise alignment; available at www.ebi.ac.uk). For example, EMBOSS Needle may be used with a BLOSUM62 matrix, a "gap open penalty" of 10, a "gap extend penalty" of 0.5, a false "end gap penalty", an "end gap open penalty" of 10 and an "end gap extend penalty" of 0.5. In general, the "percent identity" is a function of the number of matching positions divided by the number of positions compared and multiplied by 100. For instance, if 6 out of 10 sequence positions are identical between the two compared sequences after alignment, then the identity is 60%. The % identity is typically determined over the whole length of the query sequence on which the analysis is performed. Two molecules having the same primary amino acid sequence or nucleic acid sequence are identical irrespective of any chemical and/or biological modification.

The BTN3A Antibody Fragment

In one specific embodiment, the BTN3A-binding protein of the present disclosure comprises at least a BTN3A antibody fragment having
  (i) a heavy chain variable region (VH) comprising H-CDR1 of SEQ ID NO:1, H-CDR-2 of SEQ ID NO:2, and H-CDR3 of SEQ ID NO:3; and,
  (ii) a light chain variable region (VL) comprising a L-CDR1 of SEQ ID NO:4, a L-CDR2 of SEQ ID NO:5, and a L-CDR3 of SEQ ID NO:6.

In another specific embodiment, the BTN3A-binding protein of the present disclosure comprises at least a BTN3A antibody fragment having
  (i) a heavy chain variable region (VH) comprising H-CDR1 of SEQ ID NO:1, H-CDR-2 of SEQ ID NO:2, and H-CDR3 of SEQ ID NO:3; and,
  (ii) a light chain variable region (VL) comprising a L-CDR1 of SEQ ID NO:4, a L-CDR2 of SEQ ID NO:17 and a L-CDR3 of SEQ ID NO:6.

In specific embodiments, such BTN3A antibody fragment is essentially devoid of the Fc region of an antibody, for example, it does not include the Fc fragment corresponding to the CH2 and CH3 regions of an antibody, typically it does not include the fragment delimited by the amino acid from position 238 to position 243 (using Kabat numbering).

The CDR regions of the BTN3A antibody fragment of the present disclosure are delineated using the Kabat numbering (Kabat et al., 1992, hereafter "Kabat et al."). For the ease of reading, H-CDR1, H-CDR2, H-CDR3 refer the 3 CDRs of the VH region and L-CDR1, L-CDR2, L-CDR3 refer to the 3 CDRs of the VL region. Typically, said anti-BTN3A antibody fragment is an antibody fragment with the VH and VL of mAb 103.2 as disclosed in WO2012/080351, or chimeric or humanized antibody fragment having a HCDR1 of SEQ ID NO: 1, a H-CDR-2 of SEQ ID NO:2, a H-CDR3 of SEQ ID NO:3; a L-CDR1 of SEQ ID NO:4, a L-CDR2 of SEQ ID NO:5 or SEQ ID NO:17, and a L-CDR3 of SEQ ID NO:6.

The murine mAb 103.2 is obtainable from the hybridoma accessible under CNCM deposit number I-4403.

In preferred embodiments, said BTN3A antibody fragments are scFv, Fab, or (Fab)$_2$ fragment, comprising
  (i) a heavy chain variable region (VH) comprising H-CDR1 of SEQ ID NO:1, H-CDR-2 of SEQ ID NO:2, and H-CDR3 of SEQ ID NO:3; for example, VH of SEQ ID NO:7, and,
  (ii) a light chain variable region (VL) comprising a L-CDR1 of SEQ ID NO:4, a L-CDR2 of SEQ ID NO:5, and a L-CDR3 of SEQ ID NO:6; for example, VL of SEQ ID NO:8.

In preferred embodiments, said BTN3A antibody fragments are scFv, Fab, or (Fab')$_2$ fragment, comprising
  (i) a heavy chain variable region (VH) comprising H-CDR1 of SEQ ID NO:1, H-CDR-2 of SEQ ID NO:2, and H-CDR3 of SEQ ID NO:3; for example, VH of SEQ ID NO:18, and,
  (ii) a light chain variable region (VL) comprising a L-CDR1 of SEQ ID NO:4, a L-CDR2 of SEQ ID NO:17, and a L-CDR3 of SEQ ID NO:6; for example, VL of SEQ ID NO:19.

Thus, the disclosure relates to such BTN3A antibody fragments per se with activating properties, i.e. having the following advantageous properties:
  (i) they bind to human BTN3A1 with a $K_D$ of 10 nM or less, preferably with a $K_D$ of 5 nM or less as measured by bio-layer interferometry (BLI) technology or by surface plasmon resonance, and,
  (ii) they induce the activation of γδ T cells (typically Vγ9Vδ2 T cells) in co-culture with cancer cells (such as Daudi and/or SKOV-3 cells), with an $EC_{50}$ of 10 nM or below, preferably of 1 nM or below, as measured in a CD107 degranulation assay, and/or
  (iii) they induce the activation and proliferation of γδ T cells (typically Vγ9Vδ2 T cells) within PBMCs.

Examples of such activating BTN3A antibody fragments include, but are not limited to, Fab, Fab', Fab'-SH, F(ab')$_2$, Fv, Unibody, and scFv fragments, diabodies, single domain, VHH, or nanobodies and other functional fragments which maintain the advantageous activating properties of the Fab or F(ab')$_2$ fragment.

In specific embodiments, it is a monovalent antibody fragment, such as a Fab or Fab'.

In other specific embodiments, it a bivalent antibody fragment such as a (Fab')$_2$.

In other specific embodiments, it is a scFv antibody fragment.

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites.

Single-domain antibodies or VHH are antibody fragments comprising all or a portion of the heavy chain variable domain which is mutated as compared to VH antibody fragments to be soluble.

Antibody fragments can be made by various techniques, including but not limited to proteolytic digestion of an intact antibody as well as production by recombinant host cells as described herein.

Preferably, the BTN3A antibody fragment of the present disclosure is a chimeric or humanized antibody fragment. Typically, a non-human antibody is humanized to reduce immunogenicity to humans, while having at least the same or similar affinity (or superior affinity) of the parental non-human antibody. In some embodiments, the antibodies of the present disclosure are humanized antibody fragments of the parent antibody mAb 103.2 as disclosed in WO2012/080351.

Generally, a humanized antibody comprises one or more variable domains in which, CDRs, (or portions thereof) are derived from a non-human antibody, e.g. the murine mAb 103.2, optionally with one amino acid substitution in one CDR to reduce immunogenicity, in particular in L-CDR2, such as L-CDR2 of SEQ ID NO:17 wherein an isoleucine of the murine L-CDR2 has been replaced by an alanine, and FRs (or portions thereof) are derived from the murine antibody sequences with mutations to reduce immunogenicity. A humanized antibody optionally will also comprise at least a portion of a human constant region.

In certain embodiments, an activating BTN3A antibody fragment according to the disclosure having VH and VL sequences can be used to create new activating BTN3A antibody fragments, respectively, by modifying the VH and/or VL sequences, or the constant regions attached thereto. Thus, in another aspect according to at least some embodiments of the invention, the structural features of an activating anti-BTN3A antibody fragment, are used to create structurally related activating BTN3A antibody fragment that retain at least the activating property of the activating BTN3A antibody fragment. For example, the 6 CDR regions of mAb 103.2 or its mutated version with H-CDR1 of SEQ ID NO:1, H-CDR-2 of SEQ ID NO:2, and H-CDR3 of SEQ ID NO:3; L-CDR1 of SEQ ID NO:4, L-CDR2 of SEQ ID NO:5 or SEQ ID NO:17, and a L-CDR3 of SEQ ID NO:6 can be combined recombinantly with known framework regions to create additional, recombinantly-engineered, activating anti-BTN3A antibody fragment according to at least some embodiments of the invention, as discussed above. The starting material for the engineering method is one or more of the VH and/or VL sequences of mAb 103.2 with SEQ ID NO:7 and SEQ ID NO:8 or its humanized version with SEQ ID NO:18 and SEQ ID NO:19.

The functional properties of the altered antibodies can be assessed using standard assays available in the art and/or described herein. In certain embodiments of the methods of engineering antibodies according to at least some embodiments of the invention, mutations can be introduced randomly or selectively along all or part of activating anti-BTN3A antibody fragment coding sequence and the resulting modified activating anti-BTN3A antibody fragment can be screened for binding activity and/or other desired functional properties, such as activating property.

Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

Preferably, said BTN3A antibody fragment is a humanized BTN3A antibody fragment comprising:
  (i) a heavy chain variable region of SEQ ID NO:18, and,
  (ii) a light chain variable region of SEQ ID NO:19.

More specifically, the disclosure relates to a humanized BTN3A binding antibody fragment which is a scFv fragment comprising
  (i) a heavy chain variable region of SEQ ID NO:18, and,
  (ii) a light chain variable region of SEQ ID NO:19.

The above disclosed BTN3A antibody fragments are useful in particular in methods for preparing a medicament for use in treating cancers and infectious disorders.

Such medicament includes in particular recombinant BTN3A binding protein or bispecific molecules comprising, as a binding and activating domain to BTN3A, an activating BTN3A antibody fragment as disclosed above.

Further details of such BTN3A binding protein are described hereafter.

The BTN3A Binding Protein

The BTN3A binding protein of the present disclosure comprises at least a BTN3A binding antibody fragment having
- (i) a heavy chain variable region (VH) comprising H-CDR1 of SEQ ID NO:1, H-CDR-2 of SEQ ID NO:2, and H-CDR3 of SEQ ID NO:3; and,
- (ii) a light chain variable region (VL) comprising a L-CDR1 of SEQ ID NO:4, a L-CDR2 of SEQ ID NO:5 or SEQ ID NO:17, and a L-CDR3 of SEQ ID NO:6.

Said BTN3A binding protein has advantageously the following properties:
- (i) it binds to human BTN3A1 with a $K_D$ of 10 nM or less, preferably with a $K_D$ of 5 nM or less as measured by surface plasmon resonance or by bio-layer interferometry (BLI) technology, and/or,
- (ii) it induces the activation of γδ T cells γδ T cells (typically Vγ9Vδ2 T cells) in co-culture with cancer cells (such as Daudi or SKOV-3 cells), with an $EC_{50}$ of 10 nM or below, preferably of 1 nM or below, for example of 0.1 nM or below, as measured in a CD107 degranulation assay, and/or
- (iii) it induces the activation and proliferation of γδ T cells (typically Vγ9Vδ2 T cells) within PBMCs.

In specific embodiments, the binding specificity to BTN3A and activating properties with respect to BTN3A are essentially provided by said BTN3A antibody fragment comprised in such BTN3A binding protein.

In particular, in specific embodiments, said BTN3A binding protein is a fusion protein of the following formula (I):

Ab103.2-L-X    (I)

wherein
Ab103.2 is an activating BTN3A antibody fragment, as disclosed in the previous section, for example, a scFv or Fab fragment,
L is a covalent bond or a linker, typically a peptide linker,
X is a polypeptide chain.
—X or -L-X may be fused to the N-terminal end or to the C-terminal end of at least a polypeptide chain of Ab103.2.
—X or -L-X may also be bonded with other polypeptides by disulphide bridge or other covalent linkages.

In specific embodiments, X may be selected among polypeptides used to increase half-life or stability of the protein in blood, such as Fc fragments or other immunoglobulin-derived fragments, or serum albumin.

As used herein, the term "fusion protein" refers to a recombinant protein which is obtained by genetic fusion, for example by genetic fusion of at least two gene fragments encoding separate functional domains of distinct proteins. For example, the coding region of at least the heavy chain variable region (VH) of an activating BTN3A antibody fragment of the present disclosure is genetically fused with the coding region of a polypeptide X and the corresponding light chain variable region (VL) of said activating BTN3A antibody fragment is separately provided by another coding region in order to obtain a fusion protein comprising a Fab fused to a polypeptide X.

Alternatively, the coding region of an scFv of an activating BTN3A antibody fragment of the present disclosure is genetically fused with the coding region of a polypeptide X.

According to the present disclosure, —X or L-X is not an Fc region of an antibody that is linked to the Ab103.2 antibody fragment. In particular, it is shown in the present disclosure that the full length mAb 103.2 antibody, with a natural Fc region N-terminally linked to the corresponding Fab has inhibitory properties with respect to BTN3A, contrary to the corresponding Fab region which exhibits BTN3A activating properties.

In specific embodiments, said BTN3A antibody fragment is not covalently linked to the N-terminal end of an Fc region of an immunoglobulin, similar to natural full-length antibody structure.

Typically, when Ab103.2 is an scFv fragment, for example an scFv fragment comprising VH of SEQ ID NO:7 and VL of SEQ ID NO:8 or VH of SEQ ID NO:18 and VL of SEQ ID NO:19, X may be another polypeptide chain which is fused to the N-terminal end of the scFv fragment.

Bispecific or Multispecific Molecules

In another aspect, it is further disclosed herein bispecific or multi-specific molecules comprising BTN3A binding proteins and/or the activating BTN3A antibody fragments as disclosed in the previous section.

A BTN3A binding antibody fragment can be derivatized or linked to another functional molecule, e.g., another peptide or protein (e.g., another antibody or ligand for a receptor) to generate a bispecific molecule that binds to at least two different binding sites or target molecules. The antibody fragments may in fact be derivatized or linked to more than one other functional molecule to generate multi-specific molecules that bind to more than two different binding sites and/or target molecules; such multi-specific molecules are also intended to be encompassed by the term "bispecific molecule" as used herein.

To create a bispecific molecule, the BTN3A binding antibody fragments or BTN3A binding fusion proteins as disclosed above, can be functionally linked (e.g., by chemical coupling, genetic fusion, noncovalent association or otherwise) to one or more other binding molecules, such as another antibody, antibody fragment, peptide or binding mimetic, such that a bispecific molecule results.

Accordingly, the present disclosure includes bispecific molecules comprising at least one first binding specificity for BTN3A and a second binding specificity for a second target epitope.

Examples of formats of bispecific molecules include BiTEs, dual-affinity retargeting antibodies, homodimeric "knob-in-hole" antibodies, and trifunctional antibodies. For a review of different architecture of common bispecific antibody formats comprising at least one antibody fragment of a first binding specificity, see for example the review of Sedykh et al., 2018 (Drug Design, Development and Therapy, 195-208, see FIG. 3 in particular).

Additionally, for the embodiment in which the bispecific molecule is multi-specific, the molecule can further include further binding specificities, in addition to the first and second target epitope.

In one embodiment, the bispecific molecules as disclosed herein comprise, for the first binding specificity to BTN3A target epitope, at least a BTN3A binding antibody fragment as disclosed herein, including, e.g., a Fab, Fab', F(ab')$_2$, Fv, Unibody or a single chain Fv. The antibody may also be a light chain or heavy chain dimer, or any minimal fragment thereof such as a Fv or a single chain or VHH construct as described in Ladner et al. U.S. Pat. No. 4,946,778.

Other antibodies which can be employed in the bispecific molecules disclosed herein are murine, chimeric, humanized or recombinant human monoclonal antibodies.

The bispecific molecules of the present disclosure can be prepared by conjugating the constituent binding specificities, using methods known in the art. For example, each binding-specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyl-dithio)propionate (SPDP), and sulfosuccinimidyl 4-(N-maleimidomethyl) cyclohaxane-I-carboxylate (sulfo-SMCC) (Karpovsky et al., 1984; Liu et al., 1985). Other methods include those described in Brennan et al., 1985; Glennie et al., 1987; Paulus, 1985.

Alternatively, both binding specificities can be encoded in the same vector and expressed and assembled in the same host cell.

In other embodiments, the bispecific molecule is a fusion protein of formula I, wherein X comprises another antibody fragment for another binding specificity.

A bispecific molecule of the disclosure can be a single chain molecule comprising one single chain antibody and a binding determinant, or a single chain bispecific molecule comprising two binding determinants.

Binding of the bispecific molecules to their specific targets can be confirmed by, for example, enzyme-linked immunosorbent assay (ELISA), radioimmunoassay (REA), FACS analysis, bioassay (e.g., growth inhibition and apoptosis), the Octet™ system, or Western Blot assay or SPR measurements. Each of these assays generally detects the presence of protein-antibody complexes of particular interest by employing a labelled reagent (e.g., an antibody) specific for the complex of interest.

Naturally, the bispecific (or multi-specific) molecules will be designed so as to maintain the activating properties of the original BTN3A antibody fragment.

Nucleic Acid Molecules Encoding the BTN3A Antibody Fragments, the BTN3A Binding Proteins, or Bispecific Molecules of the Disclosure Also disclosed herein are the nucleic acid molecules that encode the BTN3A antibody fragments, the BTN3A binding proteins or bispecific molecules of the present disclosure.

Examples of nucleic acid molecules are those encoding the variable light and heavy chain amino acid sequences of the BTN3A antibody fragments as disclosed in the previous section, and using the genetic code and, optionally taking into account the codon bias depending on the host cell species.

Typically, nucleic acid molecules encoding VH of SEQ ID NO:7 and VL of SEQ ID NO:8 and nucleic acid molecules encoding VH of SEQ ID NO:18 and VL of SEQ ID NO:19 are part of the present disclosure. In specific embodiment, the nucleic acid molecules encode chimeric and humanized Fab or BTN3A binding antibody fragment and comprise a VH coding sequence having respectively HCDR1 of SEQ ID NO:9, HCDR2 of SEQ ID NO:10, HCDR3 of SEQ ID NO:11, and a VL coding sequence having respectively LCDR1 of SEQ ID NO:12, LCDR2 of SEQ ID NO:13 or 20, and LCDR3 of SEQ ID NO:14.

In specific embodiment, the nucleic acid molecules encode chimeric Fab or scFv BTN3A antibody fragment and comprise VH coding sequence of SEQ ID NO:15 and VL coding sequence of SEQ ID NO:16.

In specific embodiment, the nucleic acid molecules encode humanized Fab or scFv BTN3A antibody fragment and comprise VH coding sequence of SEQ ID NO:21 and VL coding sequence of SEQ ID NO:22.

The present disclosure also pertains to nucleic acid molecules that derive from the latter sequences having been optimized for protein expression in mammalian cells, for example, CHO or HEK cell lines.

The nucleic acids may be present in whole cells, in a cell lysate, or may be nucleic acids in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art (Ausubel et al., 1988). A nucleic acid of the disclosure can be, for example, DNA or RNA and may or may not contain intronic sequences. In an embodiment, the nucleic acid may be present in a vector such as a phage display vector, or in a recombinant plasmid vector.

Nucleic acids of the disclosure can be obtained using standard molecular biology techniques. Once DNA fragments encoding, for example, VH and VL segments are obtained, these DNA fragments can be further manipulated by standard recombinant DNA techniques, for example to convert the variable region genes to full-length antibody chain genes, to Fab fragment genes or to an scFv gene.

In these manipulations, a VL- or VH-encoding DNA fragment (for example VH and VL of SEQ ID NO:15 and 16 respectively, or VH and VL of SEQ ID NO:21 and 22 respectively) is operatively linked to another DNA molecule, or to a fragment encoding another protein, such as an antibody constant region or a flexible linker. The term "operatively linked", as used in this context, is intended to mean that the two DNA fragments are joined in a functional manner, for example, such that the amino acid sequences encoded by the two DNA fragments remain in-frame, or such that the protein is expressed under control of a desired promoter.

To create an scFv gene, the VH- and VL-encoding DNA fragments are operatively linked to another fragment encoding a flexible linker, e.g., encoding the amino acid sequence (Gly4-Ser)$_3$, or (Gly4-Ser)$_4$ such that the VH and VL sequences can be expressed as a contiguous single-chain protein, with the VL and VH regions joined by the flexible linker (Bird et al., 1988; Huston et al., 1988; McCafferty et al., 1990).

Generation of Transfectomas Producing BTN3A Binding Antibody Fragments, BTN3A Binding Proteins or Bispecific Molecules The BTN3A-binding antibody fragments, the BTN3A binding proteins, or the bispecific molecules of the present disclosure can be produced in a host cell transfectoma using, for example, a combination of recombinant DNA techniques and gene transfection methods as is well known in the art (Morrison, 1985).

For example, to express the binding proteins, DNAs encoding said binding proteins can be obtained by standard molecular biology or biochemistry techniques (e.g., DNA chemical synthesis, PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that a gene is ligated into a vector such that transcriptional and translational control sequences within the vector serve their intended function of regulating the transcription and translation of the antibody gene. The expression vector and expression control sequences are chosen to be compatible with the expression host cell used. If the binding proteins include distinct polypeptide, for example one sequence encoding a VL gene of a Fab as BTN3A binding antibody fragment and another a VH gene of a Fab as BTN3A binding antibody fragment, the VH and VL encoding genes can be inserted into separate vector or, more typically, both genes are inserted into the same expression vector. The genes are inserted into the expression vector by standard methods (e.g., ligation of complementary restriction sites on the antibody gene fragment and vector, or blunt end ligation if no restriction sites are present). The VH, VL or scFv sequences of the activating BTN3A binding antibody fragment described herein can be used to create the fusion proteins of formula (I) as disclosed above, by inserting such VH, VL or scFv sequences into expression vectors already encoding the corresponding X or L-X polypeptides such that the VH, VL or scFv segment is operatively linked to the X or L-X polypeptide encoding sequence within the vector. Additionally or alternatively, the recombinant expression vector can encode a signal peptide that facilitates secretion of the respective binding proteins from a host cell.

The signal peptide can be an immunoglobulin signal peptide or a heterologous signal peptide (i.e., a signal peptide from a non-immunoglobulin protein).

In addition, the recombinant expression vectors disclosed herein carry regulatory sequences that control the expression of the binding proteins in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel's publication (Goeddel, 1990). It will be appreciated by those skilled in the art that the design of the expression vector, including the selection of regulatory sequences, may depend on such factors as the choice of the host cell to be transformed, the level of expression of protein desired, etc. Regulatory sequences for mammalian host cell expression include viral elements that direct high levels of protein expression in mammalian cells, such as promoters and/or enhancers derived from cytomegalovirus (CMV), Simian Virus 40 (SV40), adenovirus (e.g., the adenovirus major late promoter (AdMLP)), and polyoma. Alternatively, nonviral regulatory sequences may be used, such as the ubiquitin promoter or P-globin promoter. Still further, regulatory elements composed of sequences from different sources, such as the SRa promoter system, which contains sequences from the SV40 early promoter and the long terminal repeat of human T cell leukaemia virus type 1 (Takebe et al., 1988).

Additionally, the recombinant expression vectors of the present disclosure may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Selectable marker genes include the dihydrofolate reductase (DHFR) gene (for use in dhfr− host cells with methotrexate selection/amplification) and the neo gene (for G418 selection).

For expression of the binding proteins, the expression vector is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. It is theoretically possible to express the binding proteins of the present disclosure in either prokaryotic or eukaryotic host cells. Expression of recombinant proteins in eukaryotic cells, for example mammalian host cells, yeast or filamentous fungi, is discussed because such eukaryotic cells, and in particular mammalian cells, are more likely than prokaryotic cells to assemble and secrete a properly folded and immunologically active antibody.

In one specific embodiment, a cloning or expression vector according to the disclosure comprises nucleic acids encoding respectively at least VH of SEQ ID NO: 7 and VL of SEQ ID NO: 8 or nucleic acids encoding respectively at least VH of SEQ ID NO:18 and VL of SEQ ID NO:19, operatively linked to suitable promoter sequences.

Mammalian host cells for expressing the recombinant antibodies of the disclosure include Chinese Hamster Ovary (CHO cells) including dhfr− CHO cells (described in Urlaub and Chasin, 1980) used with a DHFR selectable marker (as described in Kaufman and Sharp, 1982), CHOK1 dhfr+ cell lines, NSO myeloma cells, COS cells and SP2 cells, for example GS CHO cell lines together with GS Xceed™ gene expression system (Lonza), or HEK cells. When recombinant expression vectors encoding antibody genes are introduced into mammalian host cells, the antibodies are produced by culturing the host cells for a period of time sufficient for expression of the antibody in the host cells and, optionally, secretion of the antibody into the culture medium in which the host cells are grown. Antibodies can be recovered and purified for example from the culture medium after their secretion using standard protein purification methods (Shukla et al., 2007).

In one specific embodiment, the host cell of the disclosure is a host cell transfected with an expression vector having the coding sequences for an scFv fragment, for example an scFv fragment comprising at least VH of SEQ ID NO:7 and VL of SEQ ID NO:8, or, VH of SEQ ID NO:18 and VL of SEQ ID NO:19, operatively linked to suitable promoter sequences. Typically, such expression vector encodes for an scFv comprising VH coding sequence of SEQ ID NO:15 and VL coding sequence of SEQ ID NO:16, or, VH coding sequence of SEQ ID NO:21 and VL coding sequence of SEQ ID NO:22.

The latter host cells may then be further cultured under suitable conditions for the expression and production of a BTN3A binding protein.

Alternatively, cell free expression systems may be used for the production of such BTN3A binding proteins. Typically, methods of cell-free expression of proteins or antibodies are already described (Stech et al., 2017).

Pharmaceutical Compositions

In another aspect, the present disclosure provides a composition, e.g., a pharmaceutical composition, containing an activating BTN3A antibody fragment and/or a BTN3A binding protein or bispecific molecules as disclosed above, formulated together with a pharmaceutically acceptable carrier. Such compositions may include one or a combination of (e.g., two or more different) antibody fragment, or binding protein or bispecific molecule as described above.

Pharmaceutical compositions disclosed herein also can be administered in combination therapy, i.e., combined with other agents. For example, the combination therapy can include activating BTN3A binding antibody fragment and/or a BTN3A binding protein or bispecific molecules of the present disclosure, combined with at least one anti-viral, anti-inflammatory or another anti-proliferative agent. Examples of therapeutic agents that can be used in combination therapy are described in greater detail below in the next section.

As used herein, "pharmaceutically acceptable carrier" includes any and all solvents, dispersion media, coatings, antibacterial and antifungal agents, isotonic and absorption delaying agents, and the like that are physiologically compatible. The carrier should be suitable for intravenous, intramuscular, subcutaneous, parenteral, spinal or epidermal administration (e.g., by injection or infusion). In one embodiment, the carrier should be suitable for subcutaneous route. Depending on the route of administration, the active compound, i.e., antibody fragment, BTN3A binding protein, or bispecific molecule, may be coated in a material to protect the compound from the action of acids and other natural conditions that may inactivate the compound.

Sterile phosphate-buffered saline is one example of a pharmaceutically acceptable carrier. Other suitable carriers are well-known to those in the art. (Remington and Gennaro, 1995) Formulations may further include one or more excipients, preservatives, solubilizers, buffering agents, albumin to prevent protein loss on vial surfaces, etc.

The form of the pharmaceutical compositions, the route of administration, the dosage and the regimen naturally depend upon the condition to be treated, the severity of the illness, the age, weight, and sex of the patient, etc.

The pharmaceutical compositions of the disclosure can be formulated for a topical, oral, parenteral, intranasal, intravenous, intramuscular, subcutaneous or intraocular administration and the like.

Preferably, the pharmaceutical compositions contain vehicles, which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The doses used for the administration can be adapted as a function of various parameters, and in particular as a function of the mode of administration used, of the relevant pathology, or alternatively of the desired duration of treatment.

To prepare pharmaceutical compositions, an effective amount of the antibody fragment, BTN3A binding protein or bispecific molecule may be dissolved or dispersed in a pharmaceutically acceptable carrier or aqueous medium.

The pharmaceutical forms suitable for injectable use include sterile aqueous solutions or dispersions; formulations including sesame oil, peanut oil or aqueous propylene glycol; and sterile powders or lyophilizates for the extemporaneous preparation of sterile injectable solutions or dispersions. In all cases, the form must be sterile and must be fluid to the extent that easy syringeability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

Pharmaceutically acceptable salts which may be used in the formulation include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chloro-butanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatine.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly concentrated solutions for direct injection is also contemplated, where the use of DMSO as solvent is envisioned to result in extremely rapid penetration, delivering high concentrations of the active agents to a small tumor area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

The activating BTN3A antibody fragment, the recombinant BTN3A binding protein or bispecific molecule of the disclosure may be formulated within a therapeutic mixture to comprise about 0.0001 to 1.0 milligrams, or about 0.001 to 0.1 milligrams, or about 0.1 to 1.0 or even 1.0 to about 10 milligrams per dose. Multiple doses can also be administered.

Uses and Methods of the BTN3A Binding Proteins of the Disclosure

The activating BTN3A antibody fragments, the BTN3A binding proteins and the bispecific molecules of the present disclosure have in vitro and in vivo diagnostic and therapeutic utilities.

In particular, the activating BTN3A antibody fragments, the BTN3A binding proteins or the bispecific molecules of the present disclosure can activate the cytolytic function, cytokine production and/or the proliferation of γδ T cells (e.g., Vγ9Vδ2 T cells), as shown in the CD107 degranulation assay in the presence of cancer cells such Daudi cells and/or SKOV-3. More particularly, the activating BTN3A antibody fragments, the BTN3A binding proteins or the bispecific molecules of the present disclosure can induce Vγ9Vδ2 activation, which is typically assessed by an improvement of the cytotoxicity (for example, measured by the CD107 degranulation assay) in the presence of cancer cells (such as Daudi cells and/or SKOV-3) and/or can promote Vγ9Vδ2 T cells proliferation and activation, as shown in the proliferation assay within PBMCs (see the Cell Trace Violet™ dilution assay) and in the activation assay (by following the CD25 activation marker) illustrated in herein.

These activating fragments thereby may be used to overcome the immunosuppressive mechanisms observed in cancer patients and during chronic infections or may be used to ex vivo activate γδ T cells (typically Vγ9Vδ2 T cells) of patients for their re-administration in patients.

In particular, the activating BTN3A antibody fragments, the BTN3A binding proteins and the bispecific molecules of the present disclosure may be useful in a method for inducing ex vivo, in vitro or in vivo the proliferation and/or activation of γδ T cells (typically Vγ9Vδ2 T cells). For example, said method comprises contacting an effective amount of said activating BTN3A antibody fragments, BTN3A binding proteins or the bispecific molecules as disclosed in the previous sections, with said γδ T cells (typically Vγ9Vδ2 T cells), optionally in the presence of other BTN3A expressing cells, such as BTN3A expressing tumor cells.

More specifically, these molecules can be administered to cells in culture, e.g. in vitro, or ex vivo, or in a subject, e.g., in vivo, to treat, prevent or diagnose a variety of disorders including cancer or infection disorders.

As used herein, the terms "cancer", "hyperproliferative" and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness.

The terms "cancer" or "neoplasms" include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the oesophagus.

Preferred cancers are those that are susceptible to be treated by activated γδ T cells.

Examples of cancers include, but are not limited to, haematological cancers such as B-cell lymphoid neoplasm, T-cell lymphoid neoplasm, non-Hodgkin lymphoma (NHL), B-NHL, T-NHL, chronic lymphocytic leukaemia (CLL), small lymphocytic lymphoma (SLL), mantle cell lymphoma (MCL), NK-cell lymphoid neoplasm and myeloid cell lineage neoplasm.

Examples of non-haematological cancers include, but are not limited to, colon cancer, breast cancer, lung cancer, brain cancer, prostate cancer, head and neck cancer, pancreatic cancer, bladder cancer, colorectal cancer, bone cancer, cervical cancer, liver cancer, oral cancer, oesophageal cancer, thyroid cancer, kidney cancer, stomach cancer, testicular cancer and skin cancer.

Examples of infection disorders include, but are not limited to, viral, bacterial, parasitic or fungal infections such as chronic hepatitis, lung infections, lower respiratory tract infections, bronchitis, influenza, pneumoniae and sexually transmitted diseases.

Examples of viral infections include, but are not limited to, hepatitis (HAV, HBV, HCV), herpes simplex (HSV), herpes zoster, HPV, influenza (Flu), AIDS and AIDS related complex, chickenpox (varicella), common cold, cytomegalovirus (CMV) infection, smallpox (variola), Colorado tick fever, dengue fever, ebola hemorrhagic fever, foot and mouth disease, lassa fever, measles, marburg hemorrhagic fever, infectious mononucleosis, mumps, norovirus, poliomyelitis, progressive multifocal leukencephalopathy (PML), rabies, rubella, SARS, viral encephalitis, viral gastroenteritis, viral meningitis, viral pneumonia, West Nile disease and yellow fever. Examples of bacterial infections include, but are not limited to, pneumonia, bacterial meningitis, cholera, diphtheria, tuberculosis, anthrax, botulism, brucellosis, campylobacteriosis, typhus, gonorrhea, listeriosis, lyme disease, rheumatic fever, pertussis (Whooping Cough), plague, salmonellosis, scarlet fever, shigellosis, syphilis, tetanus, trachoma, tularemia, typhoid fever, and urinary tract infections. Examples also include bacterial infections caused by *Coxiella bumetii, Brucella abortus, Tropheryma whipplei, Mycobacterium tuberculosis* and *Mycobacterium canettii.*

Examples of parasitic infections include, but are not limited to, malaria, leishmaniasis, trypanosomiasis, chagas disease, cryptosporidiosis, fascioliasis, filariasis, amebic infections, giardiasis, pinworm infection, schistosomiasis, taeniasis, toxoplasmosis, trichinellosis, and trypanosomiasis. Examples of fungal infections include, but are not limited to, candidiasis, aspergillosis, coccidioidomycosis, cryptococcosis, histoplasmosis and tinea pedis.

Accordingly, the disclosure relates to a method for treating one of the disorder disclosed above, in a subject in need thereof, said method comprising a therapeutically effective amount of activating BTN3A antibody fragments, BTN3A binding proteins or bispecific molecules as disclosed above, typically, comprising an scFv or Fab with VH of SEQ ID NO:18 and VL or SEQ ID NO:19.

The activating BTN3A antibody fragments, BTN3A binding proteins or bispecific molecules for use as disclosed above may be administered as the sole active ingredient or in conjunction with, e.g. as an adjuvant to or in combination to, other drugs e.g. interleukins, anti-viral, anti-inflammatory agents or cytotoxic, anti-proliferative, chemotherapy or anti-tumor agents, e.g. for the treatment or prevention of diseases mentioned above.

For example, the activating BTN3A antibody fragments, BTN3A binding proteins or bispecific molecules for use as disclosed above may be used in combination with chemotherapy, antineoplastic agents, or immunotherapeutic agents.

Suitable antineoplastic agents may include without limitation, alkylating agents (such as cyclophosphamide, mechloretamine, chlorambucil, melphalan, nitrosureas, temozolomide), anthracyclines (such as daunorubicin, doxorubicin, epirubicin, idarubicin, mitoxantrone, valrubicin), taxanes (such as Paclitaxel, Docetaxel), epothilones, inhibitors of Topoisomerase I (such as Irinotecan or Topotecan), inhibitors of Topoisomerase II (such as Etoposide, teniposide, or Tafluposide), nucleotide analogs and precursor analogs (such as azacitidine, azathioprine, capecitabine, cytarabine, flurouracil, gemcitabine, hydroxyurea, mercaptopurine, methotrexate, or Tioguanine), peptide antibiotics (such as carboplatin, cisplatin and oxaliplatin), retinoids (such as tretinoin, alitretinoin, bexarotene), vinca alkaloids and derivatives (such as vinblastine, vincristine, vindesine, vinorelbine), targeted therapies such as kinase inhibitors (such as Ibrutinib, Idelalisib, Erlotinib, Gefitinib, Imatinib, Vemurafenib, Vismodegib), proteasome inhibitors (such as bortezomib, carfilzomib), histone deacetylase inhibitors (such as Vorinostat or Romidepsin).

Examples of interleukins include without limitation IL-2 or IL-15.

The term "IL-2" has its general meaning and refers to the human interleukin-2.

The term "IL-15" has its general meaning and refers to the human interleukin-15.

Examples of immunotherapeutic agents include without limitation phosphoantigens (e.g. zoledronic acid or other bisphosphonates), anti-PD-1 antibodies, anti-PD-L1 antibodies, anti-BTLA antibodies and anti-CTLA-4 antibodies.

The term "PD-1" has its general meaning in the art and refers to the programmed death-1 receptor. The term "PD-1" also refers to a type I transmembrane protein, belonging to the CD28-B7 signalling family of receptors that includes CD28, cytotoxic T-lymphocyte-associated antigen 4 (CTLA-4), inducible co-stimulator (ICOS), and B- and T-lymphocyte attenuator (BTLA) (Greenwald et al., 2005; Riley and June, 2005).

The term "BTLA" has its general meaning in the art and refers to B and T lymphocyte attenuator. The term "BTLA" also refers to CD272, a member of the CD28-B7 signalling family of receptors that includes CD28, cytotoxic T-lymphocyte-associated antigen 4 (CTLA-4), inducible co-stimulator (ICOS), and programmed death-1 receptor (PD-1) (Greenwald et al., 2005; Riley and June, 2005).

The term "PD-L1" has its general meaning and refers to the programmed death-ligand 1, also known as CD274 or B7-H1 (Chemnitz et al., 2004).

The term "CTLA-4" has its general meaning and refers to cytotoxic T-lymphocyte-associated protein 4, also known as CD152 (Brunet et al., 1987).

The term "anti-PD-1 antibody" has its general meaning in the art and refers to an antibody with binding affinity to PD-1 or PD-L1 and antagonist activity to PD-1, i.e., it inhibits the signal transduction cascade related to the PD-1 and inhibits PD-1 ligand binding (PD-L1; PD-L2). Such anti-PD-1 antibody preferentially inactivates PD-1 with a greater affinity and potency, respectively, than its interaction with the other subtypes or isoforms of the CD28-B7 signalling family of receptors (CD28; CTLA-4; ICOS; BTLA). Tests and assays for determining whether a compound is a PD-1 antagonist are well known by the skilled person in the art such as described in Greenwald et al., 2005; Riley and June, 2005.

Examples of such anti-PD-1 antibody includes without limitation, nivolumab, pembrolizumab, avelumab, durvalumab, or atezolizumab.

The term "anti-BTLA antibodies" has its general meaning in the art and refers to antibodies that have binding affinity and antagonistic activity to BTLA, i.e. it can inhibit the signal transduction cascade related to the BTLA. Tests and assays for determining whether a compound is a BTLA antagonist are well known by the skilled person in the art such as described in (Greenwald et al., 2005; Riley and June, 2005).

In some embodiments, the anti-BTLA antibodies are selected from those described in the International Patent Application WO2010/106051; WO2011/014438; WO2017/144668.

In some embodiments, the anti-BTLA antibody is the BTLA antibody (BTLA 8.2) which is obtainable from the hybridoma accessible under CNCM deposit number I-4123 such as disclosed in WO2010/106051 or other anti-BTLA antibodies comprising the 6 CDRs of BTLA 8.2.

In some embodiments, the anti-BTLA antibody is mAb 4C7 disclosed in WO2011/014438.

In some embodiments, the anti-BTLA antibody is mAb 629.3 disclosed in WO2017/144668, or its humanized version or variant thereof.

In accordance with the foregoing the present disclosure provides in a yet further aspect:

A method as defined above comprising co-administration, e.g. concomitantly or in sequence, of a therapeutically effective amount of a BTN3A antibody fragment or binding protein or bispecific molecule of the disclosure, and at least one second drug substance, said second drug substance being an anti-viral or anti-proliferative agent or immunotherapeutic agents (such as anti-PD-1 or anti-BTLA antibodies), e.g. as indicated above.

Also within the scope of the present disclosure are kits consisting of the compositions (e.g., activating BTN3A antibody fragments, BTN3A binding proteins or bispecific molecules disclosed herein) and instructions for use. The kit can further contain a least one additional reagent, or one or more additional antibodies or proteins. Kits typically include a label indicating the intended use of the contents of the kit. The term label includes any writing, or recorded material supplied on or with the kit, or which otherwise accompanies the kit. The kit may further comprise tools for diagnosing whether a patient belongs to a group that will respond to an BTN3A binding protein treatment, as defined above.

Another therapeutic strategy is based on the use of the activating BTN3A antibody fragments, BTN3A binding proteins or bispecific molecules disclosed herein as agents which selectively expand and/or activate γδ T cells (typically Vγ9Vδ2 T cells), including Vγ9Vδ2 T cells isolated from a human subject.

The disclosure thus relates to a method for treating a subject in need thereof, comprising:
(a) isolating blood cells comprising γδ T cells (e.g., Vγ9Vδ2 T cells), including Vγ9Vδ2 T cells, for example PBMCs from a blood sample of a subject,
(b) expanding in vitro said γδ T cells in the presence of any one of activating BTN3A antibody fragments, BTN3A binding proteins or bispecific molecules, as disclosed herein, and at least either tumor, typically BTN3A expressing tumor cells or accessory cells,
(c) collecting the expanded γδ T cells,
(d) optionally, formulating the expanded γδ T cells and administering a therapeutically efficient amount of said γδ T cells (thus typically Vγ9Vδ2 T cells) to the subject.

The invention having been fully described is now further illustrated by the following examples, which are illustrative only and are not meant to be further limiting.

EXAMPLES

Materials and Methods
I. Experiments Performed with the Chimeric Version of 103.2 Antibody in its Different Formats (IgG, Fab and F(ab')$_2$)
1. Preparation of Fab and F(ab')$_2$ Fragments
a. Pepsin Digestion for F(ab')$_2$ Generation Immobilized pepsin in 50% slurry (Thermo Scientific kit, Cat. N° 44988) was buffer-exchanged into digestion buffer (20 mM Sodium acetate pH 4.4) by spinning down the slurry at 5000 g 2 min. The supernatant was discarded and slurry resuspended in 1 mL digestion buffer followed by another spin at 5000 g 2 min. This step was repeated additional four times (five resin washes in total). The resin was then resuspended in digestion buffer up to the original slurry volume. 103.2 chimeric antibody was buffer-exchanged into digestion buffer using 5 or 10 mL Zeba Spin column (scale dependent) and concentrated to 3 mg/mL using Vivaspin concentrator (10,000 MWCO) according to manufacturer protocol. Then, the antibody was mixed with pepsin immobilized on resin and incubated at 37° C. rotating, 1.5-2 hours.

Digestion mixtures were spin down at 5000 g 2 min. The supernatant was removed and filtered into a fresh tube using an appropriate syringe and 0.22 μm small filter (Merck Millipore, Millex Cat n° SLGV004SL). The resins were washed with 1 mL PBS, spin at 5000 g 1 min. The supernatant was removed, filtered and pooled with previous supernatant. The wash step was repeated.

Digested and filtered supernatant was purified using HiLoad 16/600 200 pg size exclusion column using 10 mM Sodium acetate, 100 mM NaCl, pH 5.5 as a mobile phase. The fractions corresponding to eluted F(ab')$_2$ fragments are pooled, concentrated and sterile filtered.

F(ab')$_2$ fragments were analysed by SDS-PAGE, analytical SEC and OD$_{280\ nm}$ reading (data not shown).
b. Papain Digestion for Fab Generation Immobilized papain in 50% slurry (Thermo Scientific kit, Cat. N° 20341) was buffer-exchanged into digestion buffer (20 mM Sodium Phosphate, 10 mM EDTA, 150 mM Cysteine pH 7.0) by spinning down the slurry at 5000 g 2 min. The supernatant was discarded and slurry resuspended in larger volume of digestion buffer followed by another spin at 5000 g 2 min. This step was repeated additional four times (five resin washes in total). The resin was then resuspended in digestion buffer up to the original slurry volume.

103.2 chimeric antibody was buffer-exchanged into digestion buffer using 5 or 10 mL Zeba Spin column (scale dependent) and concentrated to 3 mg/mL using Vivaspin concentrator (10,000 MWCO) according to manufacturer protocol. Then, the antibody was mixed with papain immobilized on resin and incubated at 37° C. rotating, 42 hours.

Digestion mixture was spun down at 5000 g 2 min. The supernatant was removed and filtered into a fresh tube using an appropriate syringe and 0.22 μm small filter (Merck Millipore, Millex Cat n° SLGV004SL). The resin was washed three times with PBS, spin at 5000 g 1 min, collecting and pooling at each cycle the supernatant. Pooled fractions were then filtered into a fresh tube using an appropriate syringe and 0.22 μm small filter.

Digested and filtered supernatant was first buffer-exchanged into 1×DPBS, pH 7.4, then first purified using protein A column to remove Fc and undigested mAbs, followed by polishing step using size-exclusion (SEC) column with 10 mM sodium acetate, 100 mM NaCl, pH 5.5 as a mobile phase. The fractions corresponding to eluted Fab fragments were pooled, concentrated and sterile filtered.

Fab fragments were analysed by SDS-PAGE, analytical SEC and OD$_{280\ nm}$ reading (data not shown).
2. Affinity Measurement of Chimeric 103.2 Fab and F(Ab')$_2$ Fragments Using Biacore In order to assess the affinity of chimeric 103.2 Fab and F(ab')$_2$ binding to human BTN3A1, single cycle kinetic analysis was performed using a Biacore T200 (serial no. 1909913) instrument running Biacore T200 Control software V2.0.1 and Evaluation software V3.0 (GE Healthcare, Uppsala, Sweden). All single cycle kinetic experiments were run at 25° C. with HBS-P+ running buffer (pH 7.4) containing 0.1% BSA (GE Healthcare, Little Chalfont, UK).

Human BTN3A1 His-tagged antigen (Sino Biological, Beijing, China) was diluted in running buffer to a final concentration of 0.4 μg/mL. At the start of each cycle, BTN3A1-His was captured onto Fc2 of CM5 sensor chip pre-coupled using a His capture kit (GE Healthcare, Little Chalfont, UK) with standard amine chemistry at a flow rate of 10 μL/min. An immobilization level (RL) of ~17 RU or 8 RU, the different theoretical values to obtain a R$_{Max}$ of ~25 RU was used for the analytes Fab and F(ab')$_2$ respectively. The surface was then allowed to stabilize. Single cycle kinetics data was obtained with the purified samples (Fab and F(ab')$_2$)) at a flow rate of 40 μL/min to minimize any potential mass transfer effects. The signal from the reference channel Fc1 (no antigen capture) was subtracted from that of Fc2 to correct for differences in non-specific binding to the reference surface. A five point, three-fold dilution range from 0.617 nM to 50 nM for all samples without regeneration between each concentration was used. The signal for BTN3A1-His blank runs (no analyte) were subtracted to correct for differences in surface stability. The association phase for the five injections of increasing concentrations was monitored for 240 seconds each time and a single dissociation phase was measured for 2000 seconds following the last injection of analyte. Regeneration of the chip surface was conducted using two injections of 10 mM glycine-HCL pH 1.5 followed by a stabilization period of 240 seconds.

Raw sensorgrams were fitted with a 1:1 model for Fab samples and with a bivalent analyte model for F(ab')$_2$ samples in agreement with the different valences of the analytes. Kinetic constants obtained are detailed in Table 1 and Table 2.

3. Efficacy of Chimeric 103.2 (IgG, Fab and F(Ab')₂) in Vγ9Vδ2 T Cell Degranulation Assay The assay consists of measuring activating or inhibitory effect of chimeric antibody 103.2 and its Fab and F(ab')₂ formats on Vγ9Vδ2 T cell degranulation against Daudi Burkitt's lymphoma cell line (Harly et al., 2012). Vγ9Vδ2 T cells were expanded from PBMCs of healthy donors by culturing with zoledronic acid (1 pM) and IL-2 (200 UI/mL) for 11-13 days. IL-2 is added at day 5, day 8 and every 2 days thereafter. The percentage of Vγ9Vδ2 T cells was determined at the initiation of culture and assessed for the time of culture by flow cytometry until it reached at least 80%. At this step, Vγ9Vδ2 T cells were frozen and stored. Frozen Vγ9Vδ2 T cells were then used in degranulation assays against Daudi cell line (E:T ratio of 1:1), whereby the cells are co-cultured for 4 hours at 37° C. in presence of 10 μg/mL of 103.2 chimeric antibody and its different formats. Activation by PMA (20 ng/mL) plus Ionomycin (1 μg/mL) served as positive control for Vγ9Vδ2 T cell degranulation, and medium alone as negative control. At the end of 4 hours of co-incubation, cells were analysed by flow cytometry to evaluate the percentage of Vγ9Vδ2 T cells positive for CD107a (LAMP-1, lysosomal-associated membrane protein-1)+CD107b (LAMP-2). CD107 is mobilized to the cell surface following activation-induced granule exocytosis, thus measurement of surface CD107 is a sensitive marker for identifying recently degranulated cytolytic T cells.

Results obtained are described in Table 3.

II. Humanization of 103.2 Antibody

1. Design and Construction of the Different Humanized Variants a. Design of Humanized Variable Region Sequences Structural models of the murine 103.2 antibody V regions were produced using Swiss PDB and analysed in order to identify important "constraining" amino acids in the V regions that were likely to be essential for the binding properties of the antibody. Most residues contained within the CDRs (using both Kabat and Chothia definitions) together with a number of framework residues were considered to be important. The VH and Vκ sequences of murine 103.2 contain typical framework residues and the CDR 1, 2 and 3 motifs are comparable to many murine antibodies.

From the above analysis, it was considered that humanized sequences of 103.2 could be created with a wide latitude for alternative residues outside of the CDRs but with only a narrow menu of possible residues within the CDR sequences. Preliminary analysis indicated that corresponding sequence segments from several human antibodies could be combined to create CDRs similar, or identical, to those in the murine sequences. For regions outside of, and flanking, the CDRs, a wide selection of human sequence segments were identified as possible components of the novel humanized V regions.

b. CD4+ T Cell Epitope Avoidance

Based upon the structural analysis, a large preliminary set of sequence segments that could be used to create 103.2 humanized variants were selected and analysed using iTope™ technology for in silico analysis of peptide binding to human MHC class II alleles (Perry et al., 2008), and using the TCED™ of known antibody sequence-related T cell epitopes (Bryson et al., 2010). Sequence segments that were identified as significant non-human germline binders to human MHC class II or that scored significant hits against the TCED™ were discarded. This resulted in a reduced set of segments, and combinations of these were again analysed, as above, to ensure that the junctions between segments did not contain potential T cell epitopes. Selected sequence segments were assembled into complete V region sequences that were devoid of significant T cell epitopes. Five heavy chain (VH1 to VH5) and four light chain (Vκ1 to Vκ4) sequences were then chosen for gene synthesis and expression in mammalian cells.

c. Construction of 103.2 Humanized Variants 103.2 humanized variants were synthesized with flanking restriction enzyme sites for cloning into an expression vector system for human IgG4 (S241P, L248E) heavy and kappa light chains. The VH regions were cloned between the Mlu I and Hind III restriction sites, and the Vκ regions were cloned between the BssH II and BamH I restriction sites. All constructs were confirmed by sequencing.

2. Expression of the Antibodies

Chimeric 103.2 (VH0/Vκ0), two control combinations (VH0/Vκ1, VH1/Vκ0) and combinations of humanized heavy and light chains (a total of 23 pairings) were transiently transfected into FreeStyle™ CHO-S cells (ThermoFisher, Loughborough, UK) using a MaxCyte STX® electroporation system (MaxCyte Inc., Gaithersburg, USA) from corresponding endotoxin-free DNA. Transfections were undertaken for each antibody using OC-400 processing assemblies. Following cell recovery, cells were diluted to 3×10⁶ cells/mL into CD Opti-CHO medium (ThermoFisher, Loughborough, UK) containing 8 mM L-Glutamine (ThermoFisher, Loughborough, UK) and 1×Hypoxanthine-Thymidine (ThermoFisher, Loughborough, UK). 24 hours post-transfection, the culture temperature was reduced to 32° C. and 1 mM sodium butyrate (Sigma, Dorset, UK) was added. Cultures were fed daily by the addition of 3.6% (of the starting volume) feed (2.5% CHO CD Efficient Feed A (ThermoFisher, Loughborough, UK), 0.5% Yeastolate (BD Biosciences, Oxford, UK), 0.25 mM Glutamax (ThermoFisher, Loughborough, UK) and 2 g/L Glucose (Sigma, Dorset, UK). IgG supernatant concentrations were monitored by IgG ELISA and transfections were cultured for up to 14 days prior to harvesting supernatants.

3. Preliminary Selection: Single Cycle Kinetic Analysis of 103.2 Humanized Variants Binding to Human BTN3A1

In order to assess the binding of all 103.2 humanized variants and to select antibodies with the highest affinity to human BTN3A1, single cycle kinetic analysis was performed on supernatants from transfected cell culture using a Biacore T200 (serial no. 1909913) running Biacore T200 Evaluation Software V2.0.1 (Uppsala, Sweden).

Antibodies were diluted in 2% BSA/PBS to a final concentration of 2 μg/mL based on concentrations obtained from the supernatant titration by ELISA. At the start of each cycle, antibodies were loaded onto Fc2, Fc3 and Fc4 of the Protein A chip (GE Healthcare, Little Chalfont, UK). IgGs were captured at a flow rate of 10 μL/min to give an immobilization level (RL) of ~146.5 RU, the theoretical value to obtain $R_{Max}$ of ~50 RU. The surface was then allowed to stabilize. Single cycle kinetic data was obtained with BTN3A1-His as the analyte (Sino Biological Cat. No. 15973-H08H) at a flow rate of 30 μL/min to minimize any potential mass transfer effects, as well as using HBS-P+(GE Healthcare, Little Chalfont, UK) as running buffer. Multiple repeats with the chimeric antibody were performed to check the stability of the surface and analyte over the kinetic cycles. The signal from the reference channel Fc1 (no antibody) was subtracted from that of Fc2, Fc3 and Fc4 to correct for differences in non-specific binding to the reference surface. A three point, four-fold dilution range from 1.56 nM to 25 nM BTN3A1 without regeneration between each concentration was used. The association phase for the three injections of increasing concentrations of BTN3A1 was monitored for 240 seconds each time and a single dissociation phase was measured for 2000 seconds following the last injection of BTN3A1. Regeneration of the Protein A surface was conducted using two injections of 10 mM glycine-HCL pH 1.5 followed by a stabilization period of 240 seconds.

The signal from each antibody blank run (no BTN3A1) was subtracted to correct for differences in surface stability.

4. Purification of the Selected Antibodies

Six 103.2 humanized variants with the best affinities and best iTope™ scores were selected for further analysis.

The isoelectric point (pI) was also calculated for each of the six 103.2 humanized variants based on their corresponding amino acid sequences.

The six 103.2 selected humanized variants (VH4A/Vκ2, VH4/Vκ3, VH4/Vκ4, VH5/Vκ2, VH5/Vκ3, VH5/Vκ4) together with VH0/Vκ0 chimeric and the most conservatively humanized variant (VH1A/Vκ1) were subjected to purification for further assay testing. Antibodies were purified from cell culture supernatants on Protein A sepharose columns followed by Size Exclusion Chromatography (SEC) (GE Healthcare, Little Chalfont, UK) using 10 mM sodium acetate, 100 mM NaCl, pH 5.5 as mobile phase and final formulation buffer. Samples were quantified by $OD_{280\,nm}$ using an extinction coefficient ($Ec_{(0.1\%)}$) based on the predicted amino acid sequence.

Antibodies were analysed using SDS-PAGE by loading 2 μg of each antibody on the gel (data not shown).

5. Characterization of the Selected Humanized Variants a. Competition ELISA Analysis Purified variants were tested for their binding to recombinant human BTN3A1-His (Sino Biological cat. no. 15973-H08H) while competing against the corresponding murine antibody, 103.2. Chimeric (VH0/Vκ0) and irrelevant human IgG4 (S241P, L248E) were tested on each plate for comparison.

BTN3A1 was diluted in 1×PBS to 0.5 μg/ml and 100 μL/well was coated overnight at 4° C. on a 96-well ELISA plate. The following day, the plate was washed 3× with 1×PBS/0.05% Tween (PBS-T) and blocked with 200 μL of 2% milk/PBS for 1 hour at room temperature. In a dilution 96-well plate a fixed concentration of murine antibody 103.2 (0.15 μg/mL final concentration) was added in equal volume to a four-fold titration series of test antibody (starting from 80 μg/mL (40 μg/mL final concentration) diluted in blocking buffer). After washing the Nunc ELISA plate 3× with PBS-T, 100 μL of murine/test antibody mix was added to the ELISA plate. After one hour incubation at room temperature, the plate was washed 3 times with PBS-T and 100 μL of anti-mouse Fc HRP-labelled secondary antibody (Sigma, Dorset, UK) diluted 1:1000 in blocking buffer was applied for 1 hour at room temperature to detect bound murine antibody. The plate was washed 3 times with PBS-T following which 100 μL of TMB substrate was added and incubated for five minutes at room temperature. The reaction was stopped with 100 μl of 3.0 M hydrochloric acid and absorbance was read immediately using a Dynex plate reader at 450 nm.

The results were plotted, $IC_{50}$ values were calculated for each variant and relative $IC_{50}$ values were calculated by dividing the $IC_{50}$ of the humanized variant by that of the chimeric antibody assayed on the same plate (data not shown).

b. Thermostability Analysis

In order to assess the thermostability of the six selected 103.2 humanized variants, melting temperatures (the temperature at which 50% of a protein domain is unfolded) were determined using a fluorescence-based thermal shift assay.

All six purified 103.2 humanized antibodies, together with the chimeric (VH0/Vκ0) antibody and the humanized variant (VH1/Vκ1), were diluted to a final concentration of 0.1 mg/mL in formulation buffer (10 mM sodium acetate, 100 mM NaCl, pH 5.5) containing SYPRO® Orange (ThermoFisher, Loughborough, UK) at 1 in 1000 dilution and subjected to a temperature gradient from 25° C. to 99° C. on a StepOnePlus real-time PCR system (ThermoFisher, Loughborough, UK) over a period of 56 minutes. 10 mM sodium acetate, 100 mM NaCl, pH 5.5 was used as a negative control. The melting curves were analysed using protein thermostability software (version 1.2) (data not shown).

c. Multi Cycle Kinetic Analysis

Multi-cycle kinetic analysis was performed on the six selected humanized 103.2 variants (VH4A/Vκ2, VH4/Vκ3, VH4/Vκ4, VH5/Vκ2, VH5/Vκ3, VH5/Vκ4) together with the chimeric antibody and the humanized variant, VH1/Vκ1, using a Biacore T200 (serial no. 1909913) instrument running Biacore T200 Evaluation Software V2.0.1 (Uppsala, Sweden).

Purified antibodies were diluted to a concentration of 2 μg/mL in 2% BSA/PBS. At the start of each cycle, each antibody was captured on the Protein A at a density (RL) of 146.5 RU (theoretical value to obtain an $R_{Max}$ of ~50 RU). Following capture, the surface was allowed to stabilize before injection of the BTN3A1 antigen (Sino Biological cat. no. 15973-H08H). BTN3A1 was titrated in 0.1% BSA/HBS-P+(running buffer) in a two-fold dilution range from 12 to 0.375 nM. The association phase was monitored for 360 seconds and the dissociation phase for 45 minutes (2700 seconds). Kinetic data was obtained using a flow rate of 40 μL/min to minimize any potential mass transfer effects. Regeneration of the Protein A surface was conducted using two injections of 10 mM glycine-HCL pH 1.5 at the end of each cycle. Two blanks (no BTN3A1) and a repeat of a single concentration of the analyte were performed for each tested antibody to check the stability of the surface and analyte over the kinetic cycles. The chimeric antibody was run twice. The signal from the reference channel Fc1 was subtracted from that of Fc2, Fc3 and Fc4 to correct for differences in non-specific binding to a reference surface. Additionally, blank runs were subtracted for each Fc to correct any antigen-independent signal variation, such as drift. Sensorgrams were fitted using a one-to-one binding mathematical model with a global $R_{Max}$ parameter and no bulk signal (Constant RI=0 RU).

The relative $K_D$ compared to 103.2 chimeric (VH0/Vκ0) was calculated by dividing the $K_D$ of the 103.2 humanized variants by that of the chimeric on the same chip (data not shown).

d. Binding Assay on Human PBMCs

Humanized variants were characterized for their binding to human PBMCs, isolated from blood of healthy donors. PBMCs were isolated from buffy coats using Lymphoprep (Axis-shield, Dundee, UK) density centrifugation. PBMCs were then frozen and stored at −80° C. or in liquid nitrogen until required.

100 μL cells at 1×10⁶ cells/mL were transferred to each well of a fresh U-shaped bottom 96-well plate, then the plate was centrifuged and supernatant discarded.

A serial dilution of the antibodies, 0.001 μg/mL to 150 μg/mL was prepared in PBS 2 mM EDTA. Human PBMCs were resuspended in 50 μL of the diluted test antibody titration series prepared.

After incubation for 30 minutes at 4° C. in the dark, the plate was centrifuged and pellets washed twice with 150 μL/well of PBS 2 mM EDTA, following which the pellets were resuspended in 50 μL of a mix composed of goat anti-human antibody (PE-labelled) diluted 1/100 and Live/dead neat IR diluted 1/500 in PBS 2 mM EDTA.

After incubation for 15 minutes at 4° C. in the dark, the plate was centrifuged and pellets washed once with 150 μL/well with PBS 2 mM EDTA, following which the pellets were resuspended in 200 μL PBS 2 mM EDTA. Cells were analysed on a BD LSR Fortessa Cytometer. Data was analyzed using a FlowJo software (Version 10, FlowJo, LLC, Ashland, USA—data not shown).

e. Vγ9Vδ2 T Cell Degranulation Assay

Same protocol as described in section I. 3. was used.

Altogether, the results obtained in binding assays, thermostability studies and functional tests allowed to select the reference humanized candidate: 103.2 VH4/Vκ4 IgG1 L247F L248E P350S with C-terminal depleted lysine (as numbered under Kabat nomenclature), also named herein hu103.2.

III. Experiments Performed with the Humanized Version of 103.2 Antibody (Hu103.2) in its Different Formats (IgG, Fab and F(Ab')$_2$)

All the following experiments were performed using the reference humanized candidate that was selected after the humanization process, corresponding to 103.2 VH4/Vκ4 IgG1 L247F L248E P350S dK, also named herein hu103.2.

1. Preparation of Fab and F(Ab')$_2$ Fragments

Same protocol was used as described in section I. 1.

2. Affinity Measurement of Humanized Version of 103.2 Antibody (Hu103.2) (IgG, Fab and F(Ab')$_2$) Using Biacore In order to assess the affinity of the reference humanized 103.2 antibody (hu103.2) for human BTN3A1 in its different formats (Fab, F(ab')$_2$ and IgG), single cycle kinetic analysis was performed using a Biacore T200 (serial no. 1909913) instrument running Biacore T200 Control software V2.0.1 and Evaluation software V3.0 (GE Healthcare, Uppsala, Sweden). All single cycle kinetic experiments were run at 25° C. with HBS-P+ running buffer (pH 7.4) containing 0.1% BSA (GE Healthcare, Little Chalfont, UK).

Human BTN3A1 His-tagged antigen (Sino Biological, Beijing, China) was diluted in running buffer to a final concentration of 0.4 μg/mL. At the start of each cycle, human BTN3A1-His was captured onto Fc2 of CM5 sensor chip pre-coupled using a His capture kit (GE Healthcare, Little Chalfont, UK) with standard amine chemistry at a flow rate of 10 μL/min. An immobilization level (RL) of ~34 RU, 16 RU or 11 RU, the different theoretical values to obtain a $R_{Max}$ of ~50 RU was used for the analytes Fab, F(ab')$_2$ and IgG respectively. The surface was then allowed to stabilize. Single cycle kinetic data was obtained with the purified samples (Fab, F(ab')$_2$ and IgG) at a flow rate of 40 μL/min to minimize any potential mass transfer effects. The signal from the reference channel Fc1 (no antigen capture) was subtracted from that of Fc2 to correct for differences in non-specific binding to the reference surface. The signal for human BTN3A1-His blank runs (no analyte) were subtracted to correct for differences in surface stability. The association phase for the five injections of increasing concentrations was monitored for 240 seconds each time and a single dissociation phase was measured for 1400 seconds following the last injection of analyte. Regeneration of the chip surface was conducted using two injections of 10 mM glycine-HCL pH 1.5 followed by a stabilization period of 240 seconds.

Raw sensorgrams were fitted with a 1:1 model for Fab samples and with a bivalent analyte model for F(ab')$_2$ and IgG samples in agreement with the different valences of the analytes.

Kinetic values obtained are listed in Table 4, Table 5 and Table 6.

3. Affinity Measurement of Humanized Version of 103.2 Antibody (Hu103.2) (IgG, Fab and F(Ab')$_2$) Using Octet™

In order to assess the affinity of lead humanized 103.2 antibody for human BTN3A1 in its different formats (Fab, F(ab')$_2$ and IgG) Bio-layer interferometry technology was used. All runs (including loading, equilibration, association/dipping of sensors into analyte, dissociation and regeneration) were performed in black 96-well plates (Greiner) at 30° C. with shaking 1000 rpm using an OctetRed96 (ForteBio). FAB2G sensors (anti human CH1; Fortebio) first hydrated with 0.2 ml kinetic buffer (PBS pH 7.4, 0.02% Tween20 and 0.1% BSA) for 10 min and then loaded with humanized version of 103.2 antibody or fragments (2 μg/mL). The association of antibody or fragments with various concentrations of human BTN3A1 (60, 30, 15, 7.5, 3.75 and 1.87 nM) was monitored for 300 s, and the dissociation was followed for typically 500 s in kinetic buffer. Fitting of the data and constant measurements were performed with the Octet Red system software (version 7.1) using the 1:1 model. A control with an irrelevant antibody was used in order to assess the absence of non-specific binding of the target protein.

Kinetic values obtained are listed in Table 7.

4. Activation and Proliferation Assay

PBMCs were isolated from 3 healthy donors, stained with CellTrace Violet dye and incubated during 5 days with 67 nM of the different humanized 103.2 formats (IgG, Fab and F(ab')'$_2$) at 37° C., 5% CO$_2$. Then, activation and proliferation of the different immune subsets were observed by flow cytometry analysis.

The results obtained are summarized in Table 8.

5. Vγ9Vδ2 T Cell Degranulation Assay

Same protocol was used as described in section I. 1. Vγ9Vδ2 T cells isolated from 3 different healthy donors were expanded and co-incubated with two different cell lines: Daudi (lymphoma cell line) and SKOV-3 (ovarian cancer cell line). Several doses of different humanized version of 103.2 (IgG, Fab and F(ab')$_2$) were tested in this assay. EC$_{50}$ values (corresponding to the concentration of fragments required to obtain 50% of the maximal effect, i. e. 50% of the maximal proportion of activated Vγ9Vδ2 T cells) obtained for each format are listed in Table 9.

Results

I. Experiments Performed with the Chimeric Version of 103.2 Fab and F(Ab')$_2$ Fragments 1. Preparation of Fab and F(Ab')$_2$ Fragments Fab and F(ab')$_2$ fragments were analysed by SDS-PAGE, analytical SEC and OD$_{280\ nm}$ reading for QC analysis. No aggregation was observed for purified Fab and F(ab')$_2$ fragments (data not shown).

2. Affinity Measurement of Chimeric 103.2 Fab and F(Ab')$_2$ Fragments Using Biacore The affinity of chimeric 103.2 Fab and F(ab')$_2$ fragments for human BTN3A1 was assessed using Biacore. The kinetic constants obtained are listed in Table 1 for F(ab')$_2$ fragment and in Table 2 for Fab fragment.

TABLE 1

Kinetic values obtained using Biacore to assess the affinity of chimeric 103.2 F(ab')$_2$ fragment for human BTN3A1

| Molecule | $k_a 1$ (1/Ms) | $k_a 2$ (1/Ms) | $k_d 1$ (1/s) | $k_d 2$ (1/s) | $R_{max}$ (RU) | Chi$^2$ (RU$^2$) |
|---|---|---|---|---|---|---|
| Chimeric 103.2 (Fab')$_2$ | $2.13 \times 10^5$ | $2.14 \times 10^2$ | $1.12 \times 10^{-3}$ | $3.41 \times 10^1$ | 61.7 | 0.048 |

TABLE 2

Kinetic values obtained using Biacore to assess the affinity of chimeric 103.2 Fab fragment for human BTN3A1

| Molecule | $k_a$ (1/Ms) | $k_d$ (1/s) | $K_D$ 1 (nM) | $R_{max}$ (RU) | Chi$^2$ (RU$^2$) |
|---|---|---|---|---|---|
| Chimeric 103.2 Fab | $5.51 \times 10^5$ | $7.82 \times 10^4$ | 1.42 | 50.3 | 0.590 |

The $K_D$ value obtained for 103.2 chimeric version in a monovalent format was in a nanomolar range.

3. Efficacy of Chimeric 103.2 (IgG, Fab and F(Ab')$_2$) in Vγ9Vδ2 T Cell Degranulation Assay The efficacy of chimeric 103.2 fragments to induce Vγ9Vδ2 T cells cytotoxicity was assessed in a degranulation assay where Vγ9Vδ2 T cells were co-incubated with Daudi cells. The proportion of Vγ9Vδ2 T cells expressing CD107 at their surface are detailed in the Table 3.

TABLE 3

Percentages of degranulating Vγ9Vδ2 T cells (CD107+ cells) against target cancer cells (Daudi cells) in presence of chimeric 103.2 antibody (10 μg/mL) in its different formats (IgG, Fab and F(ab')$_2$)

| Condition | Vγ9Vδ2 T cells only | Vγ9Vδ2 T cells + Daudi cells | Vγ9Vδ2 T cells + PMA + Ionomycin (positive control) | Vγ9Vδ2 T cells + Daudi + Human IgG4 (isotype control) | Vγ9Vδ2 T cells + Daudi + 103.2 (IgG) | Vγ9Vδ2 T cells + Daudi + 103.2 F(ab')$_2$ | Vγ9Vδ2 T cells + Daudi + 103.2 Fab |
|---|---|---|---|---|---|---|---|
| % CD107* of Vγ9Vδ2 T cells* | 5.59 | 19.07 | 75.53 | 13.67 | 6.96 | 40.83 | 66.70 |

*The numbers listed are mean values calculated with values obtained from 3 different healthy donors with doses corresponding to 10 μg/mL.

As expected, 103.2 antibody in its full-length version showed a strong antagonist effect by decreasing the fraction of degranulating Vγ9Vδ2 T cells to the level observed in unstimulated (no target, no antibody) Vγ9Vδ2 T cells.

Surprisingly, the F(ab')$_2$ and Fab formats showed the opposite effect, by enhancing Vγ9Vδ2 T cell degranulation. This effect was totally unexpected.

II. Humanization of 103.2 Antibody

1. Preliminary Selection of Humanized Variants

A total of 23 pairings of humanized VH and VL regions were designed and produced for preliminary selection.

Based on antibody affinities as assessed using Biacore, on iTope™ score and on the percentage of humanness, six 103.2 humanized variants with the best affinities and best iTope™ scores were selected for further analysis (data not shown).

2. Expression and Purification of the Selected Humanized Variants

Selected humanized variants were produced, purified and analysed by SDS-PAGE. Bands corresponding to the profile of a typical antibody were observed on SDS-PAGE.

3. Characterization of the Selected Humanized Variants

First, purified 103.2 humanized variants were tested for their binding to recombinant human BTN3A1 while competing against the murine version. All tested humanized variants had an estimated IC$_{50}$ within two-fold of chimeric (data not shown).

Then, the thermostability of the six selected 103.2 humanized variants was assessed using a fluorescence-based thermal shift assay. In this assay, all antibody variants showed two distinct unfolding events with the higher Tm increasing as the degree of humanness increased.

The affinity of the six selected 103.2 humanized variants was tested using Biacore. In this experiment, all 103.2 humanized variants demonstrated affinity within two-fold of the 103.2 chimeric antibody (data not shown).

The binding of each humanized variant was assessed by flow cytometry on human PBMCs isolated from healthy donors. The ability of each antibody to bind the membrane displayed protein was validated and EC$_{50}$ values obtained were comparable for each variant (data not shown).

Finally, a degranulation assay was performed to evaluate the efficacy of each humanized variant and the EC$_{50}$ values obtained were similar for each antibody (data not shown).

Based on all generated data, one lead humanized variant was selected for immunogenicity assessment corresponding to the VH4/Vκ4. Variable regions were grafted to an IgG1 Fc-silent portion (including the mutations L247F, L248E, P350S, dK (depletion of the C terminal lysine). The final humanized candidate antibody fragment generated was named hu103.2.

III. Experiments Done with the Humanized Version of 103.2 Antibody (Hu103.2) in its Different Formats (IgG, Fab and F(Ab')$_2$)

1. Preparation of Fab and F(Ab')$_2$ Fragments

Fab and F(ab')$_2$ fragments were analysed by SDS-PAGE, analytical SEC and OD$_{280\ nm}$ reading for QC analysis. No aggregation was observed for purified Fab and F(ab')$_2$ fragments (data not shown).

2. Affinity Measurement of the Humanized Version of 103.2 Antibody (Hu103.2) in its Different Formats (IgG, Fab and F(Ab')$_2$) Using Biacore The affinity of humanized 103.2 antibody for human BTN3A1 in its different formats (IgG, Fab and F(ab')$_2$) was assessed by Biacore. Kinetic values obtained are listed in Table 4 for the IgG format, in Table 5 for the F(ab')$_2$ fragment and in Table 6 for the Fab format.

TABLE 4

Kinetic values obtained using Biacore to assess the affinity of humanized 103.2 full-length (hu103.2) antibody for human BTN3A1

| Molecule | $k_a 1$ (1/Ms) | $k_a 2$ (1/Ms) | $k_d 1$ (1/s) | $k_d 2$ (1/s) | $R_{max}$ (RU) | Chi$^2$ (RU$^2$) |
|---|---|---|---|---|---|---|
| Humanized 103.2 (hu103.2) (IgG) | 4.30 × 10$^5$ | 9.28 | 3.52 × 10$^{-4}$ | 1.76 × 10$^1$ | 86.3 | 0.391 |

TABLE 5

Kinetic values obtained using Biacore to assess the affinity of humanized 103.2 (hu103.2) F(ab')$_2$ fragment for human BTN3A1

| Molecule | $k_a 1$ (1/Ms) | $k_a 2$ (1/Ms) | $k_d 1$ (1/s) | $k_d 2$ (1/s) | $R_{max}$ (RU) | Chi$^2$ (RU$^2$) |
|---|---|---|---|---|---|---|
| Humanized 103.2 (hu103.2) (Fab')$_2$ | 6.89 × 10$^5$ | 8.35 × 10$^1$ | 1.62 × 10$^{-3}$ | 3.59 × 10$^1$ | 85.2 | 0.386 |

TABLE 6

Kinetic values obtained using Biacore to assess the affinity of humanized 103.2 (hu103.2) Fab fragment for human BTN3A1

| Molecule | $k_a$ (1/Ms) | $k_d$ (1/s) | $K_D$ 1 (nM) | $R_{max}$ (RU) | Chi$^2$ (RU$^2$) |
|---|---|---|---|---|---|
| Humanized 103.2 (hu103.2) Fab | 1.10 × 10$^6$ | 1.38 × 10$^{-3}$ | 1.26 | 78 | 0.930 |

The $K_D$ value obtained for humanized 103.2 (hu103.2) in a monovalent format was approximatively in the nanomolar range, meaning that there was no loss of affinity during the humanization process.

3. Affinity Measurement of the Humanized Version of 103.2 Antibody (Hu103.2) in its Different Formats (IgG, Fab and F(Ab')$_2$) Using Octet The affinity of humanized 103.2 antibody for human BTN3A1 in its different formats (IgG, Fab and F(ab')$_2$) was also performed using OctetRed96. Kinetic values obtained are listed in Table 7.

TABLE 7

Kinetic values obtained using OctetRed96 to assess the affinity of humanized 103.2 fragments (IgG, Fab, F(ab')$_2$) for human BTN3A1

| Protein target | Ab fragment | $K_D$ (M) | $k_{on}$ (1/Ms) | $k_{dis}$ (1/s) | Full R$^2$ | Full Chi$^2$ |
|---|---|---|---|---|---|---|
| Human BTN3A1 | Humanized 103.2 (IgG) | 1.44 × 10$^{-9}$ | 1.94 × 10$^5$ | 2.80 × 10$^{-4}$ | 0.995 | 0.903 |
| | Humanized 103.2 (Fab) | 2.43 × 10$^{-9}$ | 1.72 × 10$^5$ | 4.19 × 10$^{-4}$ | 0.994 | 1.058 |
| | Humanized 103.2 (Fab')$_2$ | 1.23 × 10$^{-9}$ | 1.98 × 10$^5$ | 2.43 × 10$^{-4}$ | 0.995 | 1.037 |

The $K_D$ values obtained for humanized 103.2 fragments were in the nanomolar range for the different formats (IgG, Fab and F(ab')$_2$).

4. Activation and Proliferation Assay

The effect of humanized 103.2 antibody (hu103.2) in its different formats (IgG, Fab and F(ab')$_2$) on the activation and proliferation of different immune subsets within PBMCs was assessed by detecting proliferation and activation markers at the surface of different immune cells using flow cytometry.

No effect was observed on B cells, CD4 and CD8 T cells for any antibody fragments. However, both proliferation and activation was observed on Vγ9Vδ2 T cells. The CellTrace Violet division values reflecting the analysis of cell division and the proportion of cells expressing CD25 at their surface are summarized in the Table 8.

TABLE 8

Analysis of Vγ9Vδ2 T cells proliferation and activation

| Condition | Medium | Humanized 103.2 (hu103.2) (IgG) | Humanized 103.2 (hu103.2) F(ab')$_2$ | Humanized 103.2 (hu103.2) Fab |
|---|---|---|---|---|
| % CTV dilution of Vγ9Vδ2 T cells* | 10.8 | 9.5 | 42.0 | 45.3 |
| % CD25$^+$ of Vγ9Vδ2 T cells* | 13.7 | 7.9 | 43.2 | 32.7 |

*The numbers listed are mean values calculated with values obtained from 3 healthy donors While humanized 103.2 antibody (hu103.2) had no effect on Vγ9Vδ2 T cells in its full-length version, the Fab and F(ab')$_2$ fragments induced their proliferation (as shown by the increase of CTV dilution reflecting the cell divisions) and their activation (reflected by the increase of Vγ9Vδ2 T cells expressing CD25 receptor which is an activation marker).

5. Vγ9Vδ2 T Cell Degranulation Assay

The efficacy of humanized 103.2 antibody (hu103.2) in its different formats (IgG, Fab and F(ab')$_2$) was assessed in a degranulation assay. Different doses of each format were tested and EC$_{50}$ values were determined and are listed in Table 9.

TABLE 9

EC$_{50}$ values obtained for humanized 103.2 antibody (hu103.2) in its different formats (IgG, Fab and F(ab')$_2$) in a Vγ9Vδ2 T cell degranulation assay against Daudi or SKOV-3 as target cells

| Condition | hu103.2 (IgG) | hu103.2 F(ab')$_2$ | hu103.2 Fab |
|---|---|---|---|
| EC$_{50}$ (nM)*-Daudi | N.A ** | 0.0005 | 0.91 |
| EC$_{50}$ (nM)*-SKOV-3 ** | N.A ** | 0.0005 | 0.08 |

*The numbers listed are mean calculated with values obtained from 3 healthy donors.
**As expected, hu103.2 in its full-length version showed a strong antagonist effect and no EC$_{50}$ value was obtained.

hu103.2 Fab and F(ab')$_2$ fragments showed a strong agonist effect on Vγ9Vδ2 T cells with EC$_{50}$ values in a sub nanomolar range for the Fab fragment and in a sub picomolar range for the F(ab')$_2$ fragment.

Again, it is totally surprising that hu103.2 showed a strong antagonist effect as full-length antibody and an opposite effect in its Fab and F(ab')$_2$ version.

SEQUENCE LISTING

Tables 10 and 11: Brief description of useful amino acid and nucleotide sequences for practicing the invention

TABLE 10

| SEQ ID NO: | Type | Description of the sequence |
|---|---|---|
| 1 | aa | HCDR1 of mAb 103.2 (murine version) |
| 2 | aa | HCDR2 of mAb 103.2 (murine version) |
| 3 | aa | HCDR3 of mAb 103.2 (murine version) |
| 4 | aa | LCDR1 of mAb 103.2 (murine version) |
| 5 | aa | LCDR2 of mAb 103.2 (murine version) |
| 6 | aa | LCDR3 of mAb 103.2 (murine version) |
| 7 | aa | VH of mAb 103.2 (murine version) |
| 8 | aa | VL of mAb 103.2 (murine version) |
| 9 | nt | HCDR1 of mAb 103.2 (murine version) |
| 10 | nt | HCDR2 of mAb 103.2 (murine version) |
| 11 | nt | HCDR3 of mAb 103.2 (murine version) |
| 12 | nt | LCDR1 of mAb 103.2 (murine version) |
| 13 | nt | LCDR2 of mAb 103.2 (murine version) |
| 14 | nt | LCDR3 of mAb 103.2 (murine version) |
| 15 | nt | VH of mAb 103.2 (murine version) |
| 16 | nt | VL of mAb 103.2 (murine version) |
| 17 | aa | LCDR2 of mAb 103.2 VH4/Vk4 (humanized version) |
| 18 | aa | VH of mAb 103.2 VH4/Vk4 (humanized version) |
| 19 | aa | VL of mAb 103.2 VH4/Vk4 (humanized version) |
| 20 | nt | LCDR2 of mAb 103.2 VH4/Vk4 (humanized version) |
| 21 | nt | VH of mAb 103.2 VH4/Vk4 (humanized version) |
| 22 | nt | VL of mAb 103.2 VH4/Vk4 (humanized version) |
| 23 | aa | Human BTN3A1 |
| 24 | aa | Human BTN3A2 |
| 25 | aa | Human BTN3A3 |

TABLE 11

| SEQ ID NO: | Type | Description of the sequence |
|---|---|---|
| 1 | aa | SYLIH |
| 2 | aa | VINPRSGDSHYNEKFKD |
| 3 | aa | SDYGAY |
| 4 | aa | RASQSISNNLH |
| 5 | aa | YASQSIF |
| 6 | aa | QQSNSWPHT |
| 7 | aa | QVQMQQSGAEVVRPGTSVKVSCKASGYAFTSYLIHWIKQRPGQG LEWIGVINPRSGDSHYNEKFKDRTTLTADQSSSTAYMQLSSLTSDD SAVYFCARSDYGAYWGQGTLVTVSS |
| 8 | aa | DIVLTQSPVTLSVTPGDSVSLSCRASQSISNNLHWYRQKSHESPRL LIKYASQSIFGIPSRFSGSGSGTEFTLSINSVETEDFGIYFCQQSNS WPHTFGTGTKLELK |
| 9 | nt | AGTTACTTGATACAC |
| 10 | nt | GTGATTAATCCTAGAAGTGGTGATAGTCACTACAATGAGAAGTT CAAGGAC |
| 11 | nt | TCAGATTACGGGGCTTAC |
| 12 | nt | AGGGCCAGCCAAAGTATTAGCAACAACCTACAC |
| 13 | nt | TATGCTTCCCAGTCCATTTTT |
| 14 | nt | CAACAGAGTAACAGCTGGCCTCACACG |
| 15 | nt | CAGGTCCAGATGCAGCAGTCTGGAGCTGAGGTGGTAAGGCCT GGGACTTCAGTGAAGGTCTCCTGCAAGGCTTCTGGATACGCCT TCACTAGTTACTTGATACACTGGATTAAACAGAGGCCTGGACAG GGCCTTGAGTGGATTGGAGTGATTAATCCTAGAAGTGGTGATA GTCACTACAATGAGAAGTTCAAGGACAGGACAACACTGACTGC AGACCAGTCCTCCAGCACTGCCTACATGCAACTCAGCAGCCTG ACATCTGATGACTCTGCGGTCTATTTCTGTGCAAGATCAGATTA CGGGGCTTACTGGGGCCAAGGGACTCTGGTCACTGTCTCTTCA |

TABLE 11-continued

| SEQ ID NO: | Type | Description of the sequence |
|---|---|---|
| 16 | nt | GATATTGTGCTAACTCAGTCACCAGTCACCCTGTCTGTGACTCC AGGAGATAGCGTCAGTCTTTCCTGCAGGGCCAGCCAAAGTATT AGCAACAACCTACACTGGTATCGACAGAAATCACATGAGTCTCC AAGGCTTCTCATCAAGTATGCTTCCCAGTCCATTTTTGGGATCC CCTCCAGGTTCAGTGGCAGTGGATCAGGGACAGAATTCACTCT CAGTATCAACAGTGTGGAGACTGAAGATTTTGGAATTTATTTCT GTCAACAGAGTAACAGCTGGCCTCACACGTTCGGTACTGGGAC CAAGCTGGAGTTGAAA |
| 17 | aa | YASQSAF |
| 18 | aa | QVQMQQSGAEVKKPGASVKVSCKASGYAFTSYLIHWIKQRPGQG LEWIGVINPRSGDSHYNEKFKDRVTMTADQSISTAYMELSRLRSDD TAVYYCARSDYGAYWGQGTLVTVSS |
| 19 | aa | EIVLTQSPATLSVSPGERATLSCRASQSISNNLHWYQQKPGQAPR LLIKYASQSAFGIPARFSGSGSGTEFTLTISSLQSEDFAVYFCQQSN SWPHTFGQGTKLEIK |
| 20 | nt | TATGCTTCCCAGTCCGCTTTT |
| 21 | nt | CAGGTCCAGATGCAGCAGTCTGGAGCTGAGGTGAAGAAGCCTG GGGCCTCAGTGAAGGTTTCCTGCAAGGCTTCTGGATACGCCTT CACTAGTTACTTGATACACTGGATTAAACAGAGGCCTGGACAGG GCCTTGAGTGGATTGGAGTGATTAATCCTAGAAGTGGTGATAGT CACTACAATGAGAAGTTCAAGGACAGGGTCACAATGACTGCAG ACCAGTCCATCAGCACTGCCTACATGGAGCTCAGCAGGCTGAG ATCTGATGACACGGCGGTCTATTACTGTGCAAGATCAGATTACG GGGCTTACTGGGGCCAAGGGACTCTGGTCACCGTCTCCTCA |
| 22 | nt | GAAATTGTGTTGACTCAGTCACCAGCCACCCTGTCTGTGTCTCC AGGAGAAAGAGCCACCCTTTCCTGCAGGGCCAGCCAAAGTATT AGCAACAACCTACACTGGTATCAGCAGAAACCTGGCCAGGCTC CAAGGCTTCTCATCAAATATGCTTCCCAGTCCGCTTTTGGCATC CCCGCCAGGTTCAGTGGCAGTGGATCAGGGACAGAATTCACTC TCACCATCAGCAGTCTGCAGTCTGAAGATTTTGCAGTTTATTTCT GTCAACAGAGTAACAGCTGGCCTCACACGTTCGGTCAGGGGAC CAAGCTGGAGATCAAA |
| 23 | aa | MKMASFLAFLLLNFRVCLLLLQLLMPHSAQFSVLGPSGPILAMVGE DADLPCHLFPTMSAETMELKWVSSSLRQVVNVYADGKEVEDRQS APYRGRTSILRDGITAGKAALRIHNVTASDSGKYLCYFQDGDFYEK ALVELKVAALGSDLHVDVKGYKDGGIHLECRSTGWYPQPQIQWSN NKGENIPTVEAPVVADGVGLYAVAASVIMRGSSGEGVSCTIRSSLL GLEKTASISIADPFFRSAQRWIAALAGTLPVLLLLLGGAGYFLWQQ QEEKKTQFRKKKREQELREMAWSTMKQEQSTRVKLLEELRWRSI QYASRGERHSAYNEWKKALFKPADVILDPKTANPILLVSEDQRSVQ RAKEPQDLPDNPERFNWHYCVLGCESFISGRHYWEVEVGDRKE WHIGVCSKNVQRKGWVKMTPENGFWTMGLTDGNKYRTLTEPRT NLKLPKPPKKVGVFLDYETGDISFYNAVDGSHIHTFLDVSFSEALYP VFRILTLEPTALTICPA |
| 24 | aa | MKMASSLAFLLLNFHVSLLLVQLLTPCSAQFSVLGPSGPILAMVGE DADLPCHLFPTMSAETMELKWVSSSLRQVVNVYADGKEVEDRQS APYRGRTSILRDGITAGKAALRIHNVTASDSGKYLCYFQDGDFYEK ALVELKVAALGSNLHVEVKGYEDGGIHLECRSTGWYPQPQIQWSN AKGENIPAVEAPVVADGVGLYEVAASVIMRGGSGEGVSCIIRNSLL GLEKTASISIADPFFRSAQPWIAALAGTLPILLLLLAGASYFLWRQQK EITALSSEIESEQEMKEMGYAATEREISLRESLQEELKRKKIQYLTR GEESSSDTNKSA |
| 25 | aa | MKMASSLAFLLLNFHVSLFLVQLLTPCSAQFSVLGPSGPILAMVGE DADLPCHLFPTMSAETMELRWVSSSLRQVVNVYADGKEVEDRQS APYRGRTSILRDGITAGKAALRIHNVTASDSGKYLCYFQDGDFYEK ALVELKVAALGSDLHIEVKGYEDGGIHLECRSTGWYPQPQIKWSDT KGENIPAVEAPVVADGVGLYAVAASVIMRGSSGGGVSCIIRNSLLG LEKTASISIADPFFRSAQPWIAALAGTLPISLLLLAGASYFLWRQQKE KIALSRETEREREMKEMGYAATEQEISLREKLQEELKWRKIQYMAR GEKSLAYHEWKMALFKPADVILDPDTANAILLVSEDQRSVQRAEEP RDLPDNPERFEWRYCVLGCENFTSGRHYWEVEVGDRKEWHIGV CSKNVERKKGWVKMTPENGYWTMGLTDGNKYRALTEPRTNLKLP EPPRKVGIFLDYETGEISFYNATDGSHIYTFPHASFSEPLYPVFRILT LEPTALTICPIPKEVESSPDPDLVPDHSLETPLTPGLANESGEPQAE VTSLLLPAHPGAEVSPSATTNQNHKLQARTEALY |

REFERENCES

Ausubel, F. M., Brent, R., Kingston, R. E., Moore, D. D., Seidman, J. G., and Struhl, K. (1988). Current Protocols in Molecular Biology (John Wiley & Sons).

Bird, R. E., Hardman, K. D., Jacobson, J. W., Johnson, S., Kaufman, B. M., Lee, S. M., Lee, T., Pope, S. H., Riordan, G. S., and Whitlow, M. (1988). Single-chain antigen-binding proteins. Science 242, 423-426.

Blazquez, J.-L., Benyamine, A., Pasero, C., and Olive, D. (2018). New Insights Into the Regulation of Vγ9Vδ2 T Cells by BTN3A and Other BTN/BTNL in Tumor Immunity. Front. Immunol. 9.

Brennan, M., Davison, P. F., and Paulus, H. (1985). Preparation of bispecific antibodies by chemical recombination of monoclonal immunoglobulin G1 fragments. Science 229, 81-83.

Brunet, J.-F., Denizot, F., Luciani, M.-F., Roux-Dosseto, M., Suzan, M., Mattei, M.-G., and Golstein, P. (1987). A new member of the immunoglobulin superfamily—CTLA-4. Nature 328, 267-270.

Bryson, C. J., Jones, T. D., and Baker, M. P. (2010). Prediction of Immunogenicity of Therapeutic Proteins. BioDrugs 24, 1-8.

Chemnitz, J. M., Parry, R. V., Nichols, K. E., June, C. H., and Riley, J. L. (2004). SHP-1 and SHP-2 Associate with Immunoreceptor Tyrosine-Based Switch Motif of Programmed Death 1 upon Primary Human T Cell Stimulation, but Only Receptor Ligation Prevents T Cell Activation. The Journal of Immunology 173, 945-954.

Gentles, A. J., Newman, A. M., Liu, C. L., Bratman, S. V., Feng, W., Kim, D., Nair, V. S., Xu, Y., Khuong, A., Hoang, C. D., et al. (2015). The prognostic landscape of genes and infiltrating immune cells across human cancers. Nature Medicine 21, 938-945.

Glennie, M. J., McBride, H. M., Worth, A. T., and Stevenson, G. T. (1987). Preparation and performance of bispecific F(ab' gamma)2 antibody containing thioether-linked Fab' gamma fragments. The Journal of Immunology 139, 2367-2375.

Goeddel, D. V. (1990). [1] Systems for heterologous gene expression. In Methods in Enzymology, (Academic Press), pp. 3-7.

Greenwald, R. J., Freeman, G. J., and Sharpe, A. H. (2005). The B7 family revisited. Annu. Rev. Immunol. 23, 515-548.

Harly, C., Guillaume, Y., Nedellec, S., Peigné, C.-M., Mönkkönen, H., Mönkkönen, J., Li, J., Kuball, J., Adams, E. J., Netzer, S., et al. (2012). Key implication of CD277/butyrophilin-3 (BTN3A) in cellular stress sensing by a major human Vγ9Vδ2 T-cell subset. Blood 120, 2269-2279.

Huston, J. S., Levinson, D., Mudgett-Hunter, M., Tai, M. S., Novotny, J., Margolies, M. N., Ridge, R. J., Bruccoleri, R. E., Haber, E., and Crea, R. (1988). Protein engineering of antibody binding sites: recovery of specific activity in an anti-digoxin single-chain Fv analogue produced in *Escherichia coli*. PNAS 85, 5879-5883.

Kabat, E. A., Wu, T. T., Foeller, C., Perry, H. M., and Gottesman, K. S. (1992). Sequences of Proteins of Immunological Interest (DIANE Publishing).

Karpovsky, B., Titus, J. A., Stephany, D. A., and Segal, D. M. (1984). Production of target-specific effector cells using hetero-cross-linked aggregates containing anti-target cell and anti-Fc gamma receptor antibodies. Journal of Experimental Medicine 160, 1686-1701.

Kaufman, R. J., and Sharp, P. A. (1982). Construction of a modular dihydrofolate reductase cDNA gene: analysis of signals utilized for efficient expression. Mol Cell Biol 2, 1304-1319.

Liu, M. A., Kranz, D. M., Kurnick, J. T., Boyle, L. A., Levy, R., and Eisen, H. N. (1985). Heteroantibody duplexes target cells for lysis by cytotoxic T lymphocytes. PNAS 82, 8648-8652.

McCafferty, J., Griffiths, A. D., Winter, G., and Chiswell, D. J. (1990). Phage antibodies: filamentous phage displaying antibody variable domains. Nature 348, 552-554.

Morrison, S. L. (1985). Transfectomas provide novel chimeric antibodies. Science 229, 1202-1207.

Palakodeti, A., Sandstrom, A., Sundaresan, L., Harly, C., Nedellec, S., Olive, D., Scotet, E., Bonneville, M., and Adams, E. J. (2012). The molecular basis for modulation of human Vγ9Vδ2 T cell responses by CD277/butyrophilin-3 (BTN3A)-specific antibodies. J. Biol. Chem. 287, 32780-32790.

Paulus, H. (1985). Preparation and biomedical applications of bispecific antibodies. Behring Inst. Mitt. 118-132.

Perry, L. C. A., Jones, T. D., and Baker, M. P. (2008). New approaches to prediction of immune responses to therapeutic proteins during preclinical development. Drugs R D 9, 385-396.

Remington, J. P., and Gennaro, A. R. (1995). Remington: the science and practice of pharmacy (Easton, Pa.: Mack Publishing).

Riley, J. L., and June, C. H. (2005). The CD28 family: a T-cell rheostat for therapeutic control of T-cell activation. Blood 105, 13-21.

Sedykh, S. E., Prinz, V. V., Buneva, V. N., and Nevinsky, G. A. (2018). Bispecific antibodies: design, therapy, perspectives.

Shukla, A. A., Hubbard, B., Tressel, T., Guhan, S., and Low, D. (2007). Downstream processing of monoclonal antibodies—Application of platform approaches. Journal of Chromatography B 848, 28-39.

Stech, M., Nikolaeva, O., Thoring, L., Stöcklein, W. F. M., Wustenhagen, D. A., Hust, M., Dübel, S., and Kubick, S. (2017). Cell-free synthesis of functional antibodies using a coupled in vitro transcription-translation system based on CHO cell lysates. Scientific Reports 7, 12030.

Takebe, Y., Seiki, M., Fujisawa, J., Hoy, P., Yokota, K., Arai, K., Yoshida, M., and Arai, N. (1988). SR alpha promoter: an efficient and versatile mammalian cDNA expression system composed of the simian virus 40 early promoter and the R-U5 segment of human T-cell leukemia virus type 1 long terminal repeat. Mol. Cell. Biol. 8, 466-472.

Tosolini, M., Pont, F., Poupot, M., Vergez, F., Nicolau-Travers, M.-L., Vermijlen, D., Sarry, J.-E., Dieli, F., and Fournié, J.-J. (2017). Assessment of tumor-infiltrating TCRVγ9Vδ2 Vγ9Vδ2 lymphocyte abundance by deconvolution of human cancers microarrays. OncoImmunology 6, e1284723.

Urlaub, G., and Chasin, L. A. (1980). Isolation of Chinese hamster cell mutants deficient in dihydrofolate reductase activity. Proc Natl Acad Sci USA 77, 4216-4220.

The invention claimed is:

1. An isolated anti-BTN3A antibody, or a fragment thereof, having
   (i) a heavy chain variable region (VH) comprising a H-CDR1 of SEQ ID NO: 1, H-CDR-2 of SEQ ID NO:2, and H-CDR3 of SEQ ID NO:3; and,
   a light chain variable region (VL) comprising a L-CDR1 of SEQ ID NO:4, a L-CDR2 of SEQ ID NO: 17, and a L-CDR3 of SEQ ID NO: 6.

2. The anti-BTN3A antibody or fragment thereof of claim 1, comprising
   (i) a heavy chain variable region of SEQ ID NO:18, and,
   (ii) a light chain variable region of SEQ ID NO:19.

3. The anti-BTN3A antibody or fragment thereof of claim 1, which is monovalent or bivalent for its binding to BTN3A.

4. A pharmaceutical composition comprising the anti-BTN3A antibody or fragment thereof of claim 1, in combination with one or more of a pharmaceutically acceptable excipient, diluent or carrier, optionally comprising other active ingredients.

5. An expression vector for the recombinant production of an anti-BTN3A antibody or fragment thereof according to claim 1 in a host cell, comprising one or more nucleic acids encoding said anti-BTN3A antibody.

6. The expression vector according to claim 5, wherein said nucleic acids comprise the coding sequences of
   (i) a heavy chain variable region of SEQ ID NO: 18, and
   (ii) a light chain variable region of SEQ ID NO: 19.

7. A host cell comprising an expression vector according to claim 5.

8. A process for the production of the anti-BTN3A antibody or fragment thereof of claim 1, comprising: (i) culturing a host cell comprising an expression vector comprising one or more nucleic acids encoding the anti-BTN3A antibody under conditions for expression of said anti-BTN3A antibody by the host cell; optionally (ii) purifying said protein and formulating said protein.

9. The isolated anti-BTN3A antibody or fragment thereof of claim 1, wherein the $K_D$ is 5 nM or less as measured by bio-layer interferometry (BLI) technology.

* * * * *

SEQUENCE LISTING

<160> NUMBER OF SEQ ID NOS: 25

<210> SEQ ID NO 1
<211> LENGTH: 5
<212> TYPE: PRT
<213> ORGANISM: Mus musculus

<400> SEQUENCE: 1

Ser Tyr Leu Ile His
1               5

<210> SEQ ID NO 2
<211> LENGTH: 17
<212> TYPE: PRT
<213> ORGANISM: Mus musculus

<400> SEQUENCE: 2

Val Ile Asn Pro Arg Ser Gly Asp Ser His Tyr Asn Glu Lys Phe Lys
1               5                   10                  15

Asp

<210> SEQ ID NO 3
<211> LENGTH: 6
<212> TYPE: PRT
<213> ORGANISM: Mus musculus

<400> SEQUENCE: 3

Ser Asp Tyr Gly Ala Tyr
1               5

<210> SEQ ID NO 4
<211> LENGTH: 11
<212> TYPE: PRT
<213> ORGANISM: Mus musculus

<400> SEQUENCE: 4

Arg Ala Ser Gln Ser Ile Ser Asn Asn Leu His
1               5                   10

<210> SEQ ID NO 5
<211> LENGTH: 7
<212> TYPE: PRT
<213> ORGANISM: Mus musculus

<400> SEQUENCE: 5

Tyr Ala Ser Gln Ser Ile Phe
1               5

<210> SEQ ID NO 6
<211> LENGTH: 9
<212> TYPE: PRT
<213> ORGANISM: Mus musculus

<400> SEQUENCE: 6

Gln Gln Ser Asn Ser Trp Pro His Thr
1               5

<210> SEQ ID NO 7
<211> LENGTH: 115
<212> TYPE: PRT
<213> ORGANISM: Mus musculus

<400> SEQUENCE: 7

Gln Val Gln Met Gln Gln Ser Gly Ala Glu Val Val Arg Pro Gly Thr

```
 1               5                  10                 15
Ser Val Lys Val Ser Cys Lys Ala Ser Gly Tyr Ala Phe Thr Ser Tyr
                20                 25                 30

Leu Ile His Trp Ile Lys Gln Arg Pro Gly Gln Gly Leu Glu Trp Ile
                35                 40                 45

Gly Val Ile Asn Pro Arg Ser Gly Asp Ser His Tyr Asn Glu Lys Phe
            50                 55                 60

Lys Asp Arg Thr Thr Leu Thr Ala Asp Gln Ser Ser Ser Thr Ala Tyr
65                 70                 75                 80

Met Gln Leu Ser Ser Leu Thr Ser Asp Asp Ser Ala Val Tyr Phe Cys
                85                 90                 95

Ala Arg Ser Asp Tyr Gly Ala Tyr Trp Gly Gln Gly Thr Leu Val Thr
                100                105                110

Val Ser Ser
        115

<210> SEQ ID NO 8
<211> LENGTH: 107
<212> TYPE: PRT
<213> ORGANISM: Mus musculus

<400> SEQUENCE: 8

Asp Ile Val Leu Thr Gln Ser Pro Val Thr Leu Ser Val Thr Pro Gly
1               5                  10                 15

Asp Ser Val Ser Leu Ser Cys Arg Ala Ser Gln Ser Ile Ser Asn Asn
                20                 25                 30

Leu His Trp Tyr Arg Gln Lys Ser His Glu Ser Pro Arg Leu Leu Ile
                35                 40                 45

Lys Tyr Ala Ser Gln Ser Ile Phe Gly Ile Pro Ser Arg Phe Ser Gly
            50                 55                 60

Ser Gly Ser Gly Thr Glu Phe Thr Leu Ser Ile Asn Ser Val Glu Thr
65                 70                 75                 80

Glu Asp Phe Gly Ile Tyr Phe Cys Gln Gln Ser Asn Ser Trp Pro His
                85                 90                 95

Thr Phe Gly Thr Gly Thr Lys Leu Glu Leu Lys
                100                105

<210> SEQ ID NO 9
<211> LENGTH: 15
<212> TYPE: DNA
<213> ORGANISM: Mus musculus

<400> SEQUENCE: 9
agttacttga tacac                                                      15

<210> SEQ ID NO 10
<211> LENGTH: 51
<212> TYPE: DNA
<213> ORGANISM: Mus musculus

<400> SEQUENCE: 10
gtgattaatc ctagaagtgg tgatagtcac tacaatgaga agttcaagga c              51

<210> SEQ ID NO 11
<211> LENGTH: 18
<212> TYPE: DNA
<213> ORGANISM: Mus musculus

<400> SEQUENCE: 11
```

```
tcagattacg gggcttac                                                       18

<210> SEQ ID NO 12
<211> LENGTH: 33
<212> TYPE: DNA
<213> ORGANISM: Mus musculus

<400> SEQUENCE: 12
agggccagcc aaagtattag caacaaccta cac                                      33

<210> SEQ ID NO 13
<211> LENGTH: 21
<212> TYPE: DNA
<213> ORGANISM: Mus musculus

<400> SEQUENCE: 13
tatgcttccc agtccatttt t                                                   21

<210> SEQ ID NO 14
<211> LENGTH: 27
<212> TYPE: DNA
<213> ORGANISM: Mus musculus

<400> SEQUENCE: 14
caacagagta acagctggcc tcacacg                                             27

<210> SEQ ID NO 15
<211> LENGTH: 345
<212> TYPE: DNA
<213> ORGANISM: Mus musculus

<400> SEQUENCE: 15
caggtccaga tgcagcagtc tggagctgag gtggtaaggc ctgggacttc agtgaaggtc         60
tcctgcaagg cttctggata cgccttcact agttacttga tacactggat taaacagagg        120
cctggacagg gccttgagtg gattggagtg attaatccta gaagtggtga tagtcactac        180
aatgagaagt tcaaggacag gacaacactg actgcagacc agtcctccag cactgcctac        240
atgcaactca gcagcctgac atctgatgac tctgcggtct atttctgtgc aagatcagat        300
tacggggctt actggggcca agggactctg tcactgtctc ttca                         345

<210> SEQ ID NO 16
<211> LENGTH: 321
<212> TYPE: DNA
<213> ORGANISM: Mus musculus

<400> SEQUENCE: 16
gatattgtgc taactcagtc accagtcacc ctgtctgtga ctccaggaga tagcgtcagt         60
ctttcctgca gggccagcca aagtattagc aacaacctac actggtatcg acagaaatca        120
catgagtctc caaggcttct catcaagtat gcttcccagt ccattttttgg gatcccctcc       180 aggttcagtg gcagtggatc agggacagaa ttcactctca gtatcaacag tgtggagact        240
gaagattttg gaatttattt ctgtcaacag agtaacagct ggcctcacac gttcggtact        300
gggaccaagc tggagttgaa a                                                  321

<210> SEQ ID NO 17
<211> LENGTH: 7
<212> TYPE: PRT
<213> ORGANISM: Artificial Sequence
<220> FEATURE:
```

<223> OTHER INFORMATION: Synthetic humanized sequences

<400> SEQUENCE: 17

Tyr Ala Ser Gln Ser Ala Phe
1               5

<210> SEQ ID NO 18
<211> LENGTH: 115
<212> TYPE: PRT
<213> ORGANISM: Artificial Sequence
<220> FEATURE:
<223> OTHER INFORMATION: Synthetic humanized sequences

<400> SEQUENCE: 18

Gln Val Gln Met Gln Gln Ser Gly Ala Glu Val Lys Lys Pro Gly Ala
1               5                   10                  15

Ser Val Lys Val Ser Cys Lys Ala Ser Gly Tyr Ala Phe Thr Ser Tyr
                20                  25                  30

Leu Ile His Trp Ile Lys Gln Arg Pro Gly Gln Gly Leu Glu Trp Ile
            35                  40                  45

Gly Val Ile Asn Pro Arg Ser Gly Asp Ser His Tyr Asn Glu Lys Phe
        50                  55                  60

Lys Asp Arg Val Thr Met Thr Ala Asp Gln Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Asp Tyr Gly Ala Tyr Trp Gly Gln Gly Thr Leu Val Thr
                100                 105                 110

Val Ser Ser
        115

<210> SEQ ID NO 19
<211> LENGTH: 107
<212> TYPE: PRT
<213> ORGANISM: Artificial Sequence
<220> FEATURE:
<223> OTHER INFORMATION: Synthetic humanized sequences

<400> SEQUENCE: 19

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Ile Ser Asn Asn
                20                  25                  30

Leu His Trp Tyr Gln Gln Lys Pro Gly Gln Ala Pro Arg Leu Leu Ile
            35                  40                  45

Lys Tyr Ala Ser Gln Ser Ala Phe Gly Ile Pro Ala Arg Phe Ser Gly
        50                  55                  60

Ser Gly Ser Gly Thr Glu Phe Thr Leu Thr Ile Ser Ser Leu Gln Ser
65                  70                  75                  80

Glu Asp Phe Ala Val Tyr Phe Cys Gln Gln Ser Asn Ser Trp Pro His
                85                  90                  95

Thr Phe Gly Gln Gly Thr Lys Leu Glu Ile Lys
                100                 105

<210> SEQ ID NO 20
<211> LENGTH: 21
<212> TYPE: DNA
<213> ORGANISM: Artificial Sequence
<220> FEATURE:
<223> OTHER INFORMATION: Synthetic humanized sequences

<400> SEQUENCE: 20
tatgcttccc agtccgcttt t                                        21

<210> SEQ ID NO 21
<211> LENGTH: 345
<212> TYPE: DNA
<213> ORGANISM: Artificial Sequence
<220> FEATURE:
<223> OTHER INFORMATION: Synthetic humanized sequences

<400> SEQUENCE: 21
caggtccaga tgcagcagtc tggagctgag gtgaagaagc tggggcctc agtgaaggtt    60
tcctgcaagg cttctggata cgccttcact agttacttga tacactggat taaacagagg   120
cctggacagg gccttgagtg gattggagtg attaatccta gaagtggtga tagtcactac   180
aatgagaagt tcaaggacag ggtcacaatg actgcagacc agtccatcag cactgcctac   240
atggagctca gcaggctgag atctgatgac acggcggtct attactgtgc aagatcagat   300
tacggggctt actggggcca aggactctg gtcaccgtct cctca                   345

<210> SEQ ID NO 22
<211> LENGTH: 321
<212> TYPE: DNA
<213> ORGANISM: Artificial Sequence
<220> FEATURE:
<223> OTHER INFORMATION: Synthetic humanized sequences

<400> SEQUENCE: 22
gaaattgtgt tgactcagtc accagccacc ctgtctgtgt ctccaggaga aagagccacc    60
ctttcctgca gggccagcca agtattagc aacaacctac actggtatca gcagaaacct   120
ggccaggctc caaggcttct catcaaatat gcttcccagt ccgcttttgg catccccgcc   180
aggttcagtg gcagtggatc agggacagaa ttcactctca ccatcagcag tctgcagtct   240
gaagattttg cagtttattt ctgtcaacag agtaacagct ggcctcacac gttcggtcag   300
gggaccaagc tggagatcaa a                                            321

<210> SEQ ID NO 23
<211> LENGTH: 513
<212> TYPE: PRT
<213> ORGANISM: Homo sapiens

<400> SEQUENCE: 23

Met Lys Met Ala Ser Phe Leu Ala Phe Leu Leu Leu Asn Phe Arg Val
1               5                   10                  15

Cys Leu Leu Leu Leu Gln Leu Leu Met Pro His Ser Ala Gln Phe Ser
                20                  25                  30

Val Leu Gly Pro Ser Gly Pro Ile Leu Ala Met Val Gly Glu Asp Ala
            35                  40                  45

Asp Leu Pro Cys His Leu Phe Pro Thr Met Ser Ala Glu Thr Met Glu
        50                  55                  60

Leu Lys Trp Val Ser Ser Ser Leu Arg Gln Val Val Asn Val Tyr Ala
65                  70                  75                  80

Asp Gly Lys Glu Val Glu Asp Arg Gln Ser Ala Pro Tyr Arg Gly Arg
                85                  90                  95

Thr Ser Ile Leu Arg Asp Gly Ile Thr Ala Gly Lys Ala Ala Leu Arg
                100                 105                 110

Ile His Asn Val Thr Ala Ser Asp Ser Gly Lys Tyr Leu Cys Tyr Phe

```
            115                 120                 125
Gln Asp Gly Asp Phe Tyr Glu Lys Ala Leu Val Glu Leu Lys Val Ala
        130                 135                 140
Ala Leu Gly Ser Asp Leu His Val Asp Val Lys Gly Tyr Lys Asp Gly
145                 150                 155                 160
Gly Ile His Leu Glu Cys Arg Ser Thr Gly Trp Tyr Pro Gln Pro Gln
                165                 170                 175
Ile Gln Trp Ser Asn Asn Lys Gly Glu Asn Ile Pro Thr Val Glu Ala
            180                 185                 190
Pro Val Ala Asp Gly Val Gly Leu Tyr Ala Val Ala Ala Ser Val
                195                 200                 205
Ile Met Arg Gly Ser Ser Gly Glu Gly Val Ser Cys Thr Ile Arg Ser
        210                 215                 220
Ser Leu Leu Gly Leu Glu Lys Thr Ala Ser Ile Ser Ile Ala Asp Pro
225                 230                 235                 240
Phe Phe Arg Ser Ala Gln Arg Trp Ile Ala Ala Leu Ala Gly Thr Leu
                245                 250                 255
Pro Val Leu Leu Leu Leu Gly Gly Ala Gly Tyr Phe Leu Trp Gln
            260                 265                 270
Gln Gln Glu Glu Lys Lys Thr Gln Phe Arg Lys Lys Arg Glu Gln
        275                 280                 285
Glu Leu Arg Glu Met Ala Trp Ser Thr Met Lys Gln Glu Gln Ser Thr
290                 295                 300
Arg Val Lys Leu Leu Glu Glu Leu Arg Trp Arg Ser Ile Gln Tyr Ala
305                 310                 315                 320
Ser Arg Gly Glu Arg His Ser Ala Tyr Asn Glu Trp Lys Lys Ala Leu
                325                 330                 335
Phe Lys Pro Ala Asp Val Ile Leu Asp Pro Lys Thr Ala Asn Pro Ile
            340                 345                 350
Leu Leu Val Ser Glu Asp Gln Arg Ser Val Gln Arg Ala Lys Glu Pro
                355                 360                 365
Gln Asp Leu Pro Asp Asn Pro Glu Arg Phe Asn Trp His Tyr Cys Val
        370                 375                 380
Leu Gly Cys Glu Ser Phe Ile Ser Gly Arg His Tyr Trp Glu Val Glu
385                 390                 395                 400
Val Gly Asp Arg Lys Glu Trp His Ile Gly Val Cys Ser Lys Asn Val
                405                 410                 415
Gln Arg Lys Gly Trp Val Lys Met Thr Pro Glu Asn Gly Phe Trp Thr
            420                 425                 430
Met Gly Leu Thr Asp Gly Asn Lys Tyr Arg Thr Leu Thr Glu Pro Arg
        435                 440                 445
Thr Asn Leu Lys Leu Pro Lys Pro Lys Lys Val Gly Val Phe Leu
450                 455                 460
Asp Tyr Glu Thr Gly Asp Ile Ser Phe Tyr Asn Ala Val Asp Gly Ser
465                 470                 475                 480
His Ile His Thr Phe Leu Asp Val Ser Phe Ser Glu Ala Leu Tyr Pro
                485                 490                 495
Val Phe Arg Ile Leu Thr Leu Glu Pro Thr Ala Leu Thr Ile Cys Pro
                500                 505                 510
Ala

<210> SEQ ID NO 24
<211> LENGTH: 334
```

```
<212> TYPE: PRT
<213> ORGANISM: Homo sapiens

<400> SEQUENCE: 24

Met Lys Met Ala Ser Ser Leu Ala Phe Leu Leu Leu Asn Phe His Val
1               5                   10                  15

Ser Leu Leu Leu Val Gln Leu Leu Thr Pro Cys Ser Ala Gln Phe Ser
            20                  25                  30

Val Leu Gly Pro Ser Gly Pro Ile Leu Ala Met Val Gly Glu Asp Ala
        35                  40                  45

Asp Leu Pro Cys His Leu Phe Pro Thr Met Ser Ala Glu Thr Met Glu
    50                  55                  60

Leu Lys Trp Val Ser Ser Leu Arg Gln Val Val Asn Val Tyr Ala
65                  70                  75                  80

Asp Gly Lys Glu Val Glu Asp Arg Gln Ser Ala Pro Tyr Arg Gly Arg
                85                  90                  95

Thr Ser Ile Leu Arg Asp Gly Ile Thr Ala Gly Lys Ala Ala Leu Arg
            100                 105                 110

Ile His Asn Val Thr Ala Ser Asp Ser Gly Lys Tyr Leu Cys Tyr Phe
        115                 120                 125

Gln Asp Gly Asp Phe Tyr Glu Lys Ala Leu Val Glu Leu Lys Val Ala
130                 135                 140

Ala Leu Gly Ser Asn Leu His Val Glu Val Lys Gly Tyr Glu Asp Gly
145                 150                 155                 160

Gly Ile His Leu Glu Cys Arg Ser Thr Gly Trp Tyr Pro Gln Pro Gln
                165                 170                 175

Ile Gln Trp Ser Asn Ala Lys Gly Glu Asn Ile Pro Ala Val Glu Ala
            180                 185                 190

Pro Val Val Ala Asp Gly Val Gly Leu Tyr Glu Val Ala Ala Ser Val
        195                 200                 205

Ile Met Arg Gly Gly Ser Gly Glu Gly Val Ser Cys Ile Ile Arg Asn
210                 215                 220

Ser Leu Leu Gly Leu Glu Lys Thr Ala Ser Ile Ser Ile Ala Asp Pro
225                 230                 235                 240

Phe Phe Arg Ser Ala Gln Pro Trp Ile Ala Ala Leu Ala Gly Thr Leu
                245                 250                 255

Pro Ile Leu Leu Leu Leu Leu Ala Gly Ala Ser Tyr Phe Leu Trp Arg
            260                 265                 270

Gln Gln Lys Glu Ile Thr Ala Leu Ser Ser Glu Ile Glu Ser Glu Gln
        275                 280                 285

Glu Met Lys Glu Met Gly Tyr Ala Ala Thr Glu Arg Glu Ile Ser Leu
    290                 295                 300

Arg Glu Ser Leu Gln Glu Leu Lys Arg Lys Ile Gln Tyr Leu
305                 310                 315                 320

Thr Arg Gly Glu Glu Ser Ser Ser Asp Thr Asn Lys Ser Ala
                325                 330

<210> SEQ ID NO 25
<211> LENGTH: 584
<212> TYPE: PRT
<213> ORGANISM: Homo sapiens

<400> SEQUENCE: 25

Met Lys Met Ala Ser Ser Leu Ala Phe Leu Leu Leu Asn Phe His Val
1               5                   10                  15
```

```
Ser Leu Phe Leu Val Gln Leu Thr Pro Cys Ser Ala Gln Phe Ser
             20                  25                  30

Val Leu Gly Pro Ser Gly Pro Ile Leu Ala Met Val Gly Glu Asp Ala
         35                  40                  45

Asp Leu Pro Cys His Leu Phe Pro Thr Met Ser Ala Glu Thr Met Glu
     50                  55                  60

Leu Arg Trp Val Ser Ser Leu Arg Gln Val Val Asn Val Tyr Ala
 65                  70                  75                  80

Asp Gly Lys Glu Val Glu Asp Arg Gln Ser Ala Pro Tyr Arg Gly Arg
                 85                  90                  95

Thr Ser Ile Leu Arg Asp Gly Ile Thr Ala Gly Lys Ala Ala Leu Arg
                100                 105                 110

Ile His Asn Val Thr Ala Ser Asp Ser Gly Lys Tyr Leu Cys Tyr Phe
            115                 120                 125

Gln Asp Gly Asp Phe Tyr Glu Lys Ala Leu Val Glu Leu Lys Val Ala
        130                 135                 140

Ala Leu Gly Ser Asp Leu His Ile Glu Val Lys Gly Tyr Glu Asp Gly
145                 150                 155                 160

Gly Ile His Leu Glu Cys Arg Ser Thr Gly Trp Tyr Pro Gln Pro Gln
                165                 170                 175

Ile Lys Trp Ser Asp Thr Lys Gly Glu Asn Ile Pro Ala Val Glu Ala
                180                 185                 190

Pro Val Val Ala Asp Gly Val Gly Leu Tyr Ala Val Ala Ala Ser Val
        195                 200                 205

Ile Met Arg Gly Ser Ser Gly Gly Val Ser Cys Ile Ile Arg Asn
    210                 215                 220

Ser Leu Leu Gly Leu Glu Lys Thr Ala Ser Ile Ser Ile Ala Asp Pro
225                 230                 235                 240

Phe Phe Arg Ser Ala Gln Pro Trp Ile Ala Ala Leu Ala Gly Thr Leu
                245                 250                 255

Pro Ile Ser Leu Leu Leu Leu Ala Gly Ala Ser Tyr Phe Leu Trp Arg
            260                 265                 270

Gln Gln Lys Glu Lys Ile Ala Leu Ser Arg Glu Thr Glu Arg Glu Arg
        275                 280                 285

Glu Met Lys Glu Met Gly Tyr Ala Ala Thr Glu Gln Glu Ile Ser Leu
    290                 295                 300

Arg Glu Lys Leu Gln Glu Glu Leu Lys Trp Arg Lys Ile Gln Tyr Met
305                 310                 315                 320

Ala Arg Gly Glu Lys Ser Leu Ala Tyr His Glu Trp Lys Met Ala Leu
                325                 330                 335

Phe Lys Pro Ala Asp Val Ile Leu Asp Pro Asp Thr Ala Asn Ala Ile
            340                 345                 350

Leu Leu Val Ser Glu Asp Gln Arg Ser Val Gln Arg Ala Glu Glu Pro
        355                 360                 365

Arg Asp Leu Pro Asp Asn Pro Glu Arg Phe Glu Trp Arg Tyr Cys Val
    370                 375                 380

Leu Gly Cys Glu Asn Phe Thr Ser Gly Arg His Tyr Trp Glu Val Glu
385                 390                 395                 400

Val Gly Asp Arg Lys Glu Trp His Ile Gly Val Cys Ser Lys Asn Val
                405                 410                 415

Glu Arg Lys Lys Gly Trp Val Lys Met Thr Pro Glu Asn Gly Tyr Trp
            420                 425                 430

Thr Met Gly Leu Thr Asp Gly Asn Lys Tyr Arg Ala Leu Thr Glu Pro
```

-continued

```
                435                 440                 445
Arg Thr Asn Leu Lys Leu Pro Glu Pro Pro Arg Lys Val Gly Ile Phe
    450                 455                 460
Leu Asp Tyr Glu Thr Gly Glu Ile Ser Phe Tyr Asn Ala Thr Asp Gly
465                 470                 475                 480
Ser His Ile Tyr Thr Phe Pro His Ala Ser Phe Ser Glu Pro Leu Tyr
                485                 490                 495
Pro Val Phe Arg Ile Leu Thr Leu Glu Pro Thr Ala Leu Thr Ile Cys
            500                 505                 510
Pro Ile Pro Lys Glu Val Glu Ser Ser Pro Asp Pro Asp Leu Val Pro
        515                 520                 525
Asp His Ser Leu Glu Thr Pro Leu Thr Pro Gly Leu Ala Asn Glu Ser
    530                 535                 540
Gly Glu Pro Gln Ala Glu Val Thr Ser Leu Leu Leu Pro Ala His Pro
545                 550                 555                 560
Gly Ala Glu Val Ser Pro Ser Ala Thr Thr Asn Gln Asn His Lys Leu
                565                 570                 575
Gln Ala Arg Thr Glu Ala Leu Tyr
            580
```